United States Patent
Camara et al.

(10) Patent No.: US 10,139,406 B2
(45) Date of Patent: Nov. 27, 2018

(54) ALKYL QUINOLONES AS BIOMARKERS OF PSEUDOMONAS AERUGINOSA INFECTION AND USES THEREOF

(71) Applicant: The University of Nottingham, Nottingham, Nottinghamshire (GB)

(72) Inventors: Miguel Camara, Nottingham (GB); Paul Williams, Nottingham (GB); David Barrett, Nottingham (GB); Nigel Halliday, Nottingham (GB); Alan Knox, Nottingham (GB); Alan Smyth, Nottingham (GB); Andrew Fogarty, Nottingham (GB); Helen Barr, Nottingham (GB); Doug Forrester, Nottingham (GB)

(73) Assignee: The University of Nottingham, Nottingham (GB)

( * ) Notice: Subject to any disclaimer, the term of this patent is extended or adjusted under 35 U.S.C. 154(b) by 0 days.

(21) Appl. No.: 14/891,242

(22) PCT Filed: May 13, 2014

(86) PCT No.: PCT/GB2014/051458
§ 371 (c)(1),
(2) Date: Nov. 13, 2015

(87) PCT Pub. No.: WO2014/184535
PCT Pub. Date: Nov. 20, 2014

(65) Prior Publication Data
US 2016/0131648 A1 May 12, 2016

(30) Foreign Application Priority Data

May 14, 2013 (GB) .................................. 1308639.2

(51) Int. Cl.
| | | |
|---|---|---|
| *G01N 33/569* | (2006.01) | |
| *C07D 215/22* | (2006.01) | |
| *C07D 215/24* | (2006.01) | |
| *C07D 215/26* | (2006.01) | |
| *C07H 17/02* | (2006.01) | |
| *C07K 16/12* | (2006.01) | |
| *C12Q 1/04* | (2006.01) | |
| *G01N 33/84* | (2006.01) | |

(52) U.S. Cl.
CPC ..... *G01N 33/56911* (2013.01); *C07D 215/22* (2013.01); *C07D 215/24* (2013.01); *C07D 215/26* (2013.01); *C07H 17/02* (2013.01); *C07K 16/1214* (2013.01); *C12Q 1/04* (2013.01); *G01N 33/84* (2013.01); *G01N 2333/21* (2013.01); *G01N 2469/10* (2013.01)

(58) Field of Classification Search
CPC .... C12Q 1/04; G01N 33/84; G01N 33/56911; G01N 2333/21; G01N 2469/10; C07K 16/1214; C07H 17/02; C07D 215/26; C07D 215/24; C07D 215/22

See application file for complete search history.

(56) References Cited

U.S. PATENT DOCUMENTS

2004/0002130 A1* 1/2004 Pesci ..................... C12Q 1/18
435/32

OTHER PUBLICATIONS

Miguel Camara-Garcia. Marker of Pseudomonas infection in urine/blood and saliva. The University of Nottingham. 2012, pp. 1-2, web link http://uon.technologypublisher.com/technology/8851.*
Fletcher et al. Biosensor-based assays for PQS, HHQ and related 2-alkyl-4-quinolone quorum sensing signal molecules. Nature Protocols 2007, vol. 2, No. 5, pp. 1254-1262.*
Flecher et al. A dual biosensor for 2-alkyl-4-quinolone quorum-sensing signal molecules. Environmental Microbiology 1007, vol. 9, No. 11, pp. 2683-2693.*
Collier et al. A bacterial cell to cell signal in the lungs of cystic fibrosis patients. FEMS Microbiology Letters 2002, vol. 215, pp. 41-46.*
Guina et al., Quantitative proteomic analysis indicates increased synthesis of a quinolone by Pseudomonas aeruginosa isolates from cystic fibrosis airways. Proc Natl Acad Sci U S A. Mar. 4, 2003;100(5):2771-6.
Hooi et al., Differential immune modulatory activity of Pseudomonas aeruginosa quorum-sensing signal molecules. Infect Immun. Nov. 2004;72(11):6463-70.
Ortori et al., Simultaneous quantitative profiling of N-acyl-L-homoserine lactone and 2-alkyl-4(1H)-quinolone families of quorum-sensing signaling molecules using LC-MS/MS. Anal Bioanal Chem. Jan. 2011;399(2):839-50.
Palmer et al., Cystic fibrosis sputum supports growth and cues key aspects of Pseudomonas aeruginosa physiology. J Bacteriol. Aug. 2005;187(15):5267-77.
International Search Report and Written Opinion for Application No. PCT/GB2014/051458, dated Oct. 20, 2014. 14 pages.

* cited by examiner

*Primary Examiner* — Shafiqul Haq
(74) *Attorney, Agent, or Firm* — McCarter & English, LLP; Lisa D. Tyner; Wei Song

(57) ABSTRACT

A method of determining the *P. aeruginosa* or related species infection status of a subject comprising: (i) providing a sample of material obtained from the subject; (ii) determining the level of one or more alkyl quinolones or metabolites thereof produced by *P. aeruginosa* or a related species in the sample

11 Claims, 22 Drawing Sheets

| QSSM | Sputum & Plasma (N=55) | Sputum & Urine (N=58) | Plasma & Urine (N=56) |
|---|---|---|---|
| HHQ | 0.72<br><0.0001 | 0.63<br><0.0001 | 0.80<br><0.0001 |
| NHQ | 0.49<br><0.001 | 0.65<br><0.0001 | 0.54<br><0.0001 |
| HQNO | 0.56<br><0.0001 | 0.61<br><0.0001 | 0.63<br><0.0001 |
| NQNO | 0.58<br><0.0001 | 0.13<br>0.34 | 0.32<br>0.02 |

Figures 3, 4:
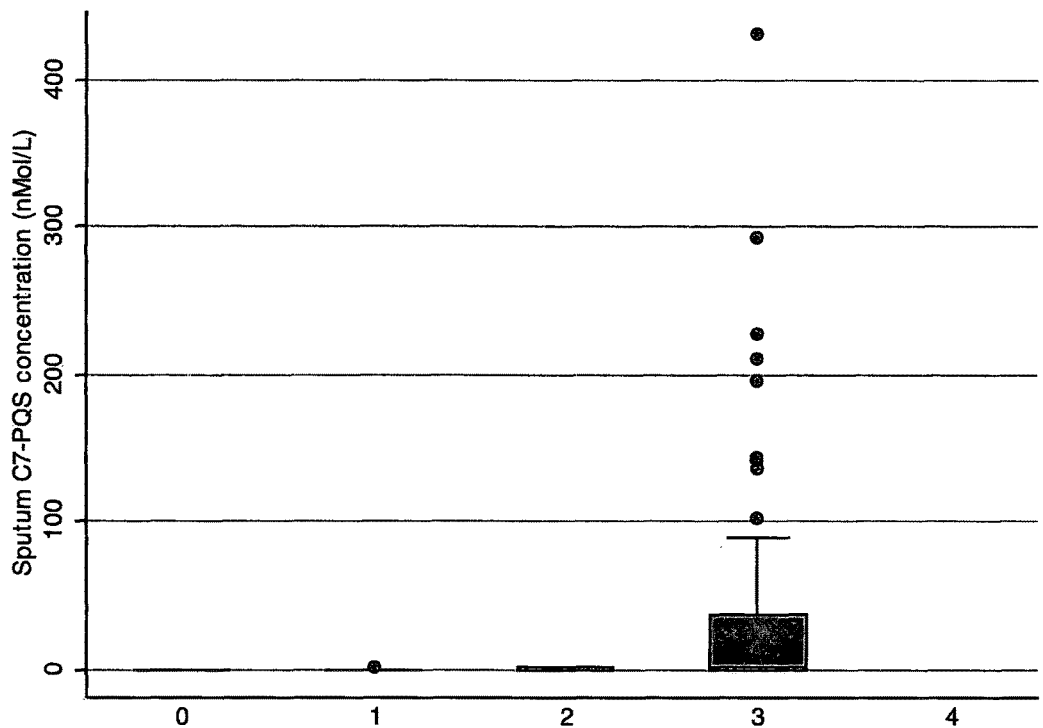

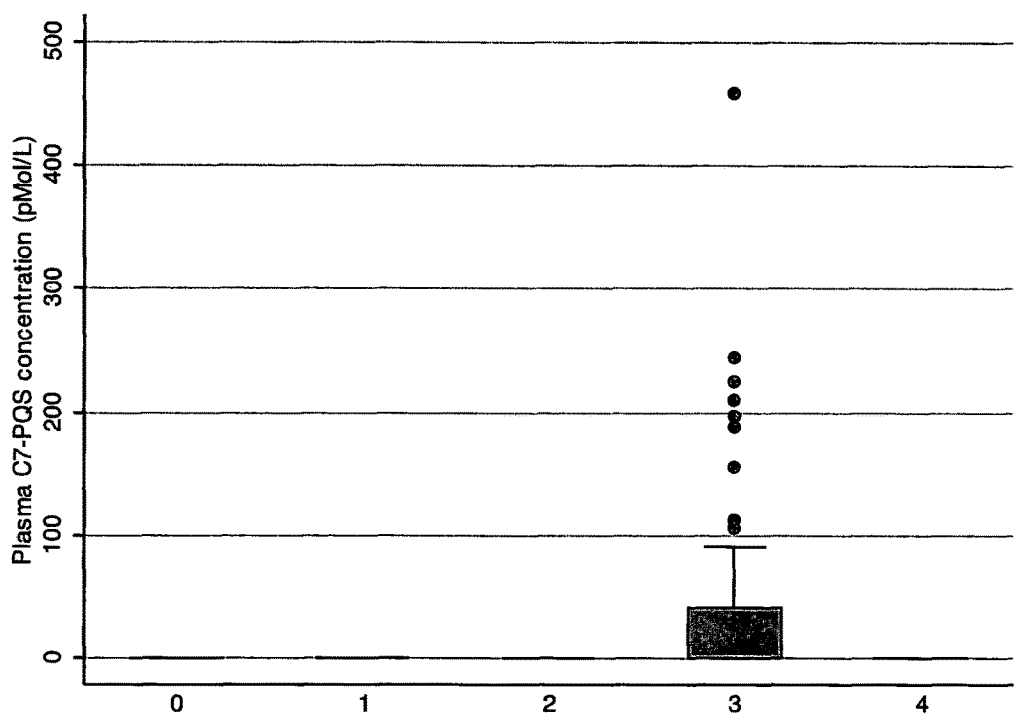
Figure 4 (ii)
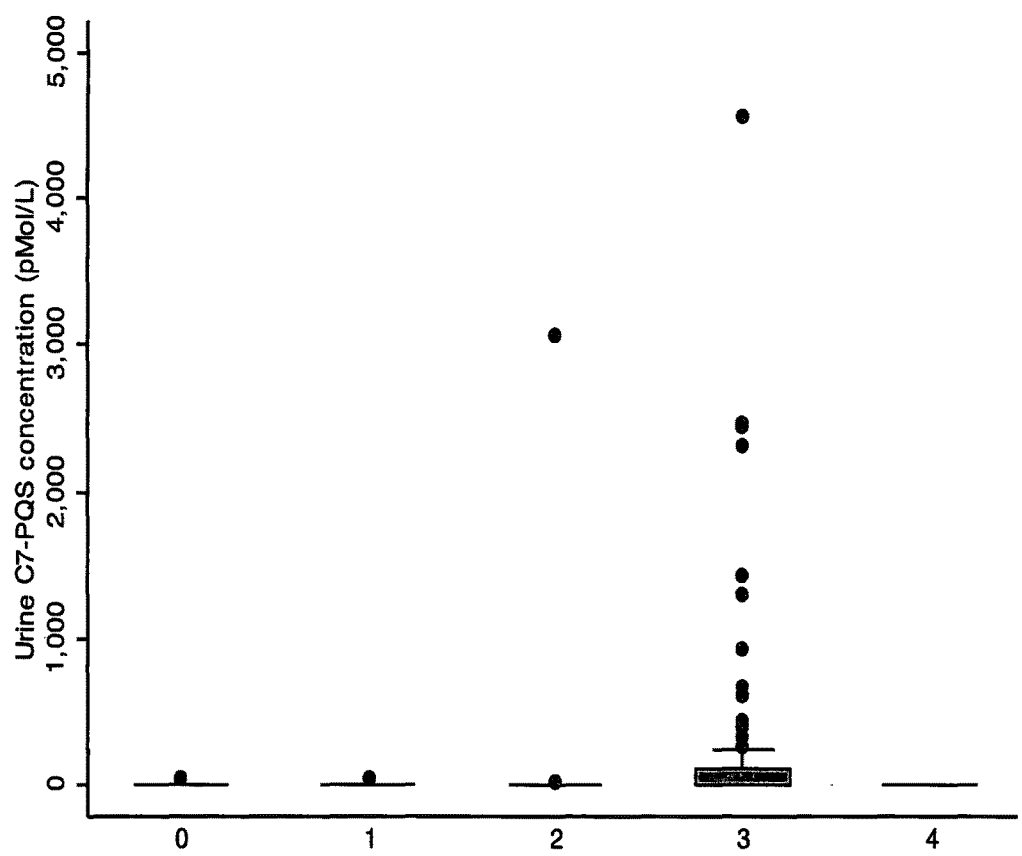
Figure 4 (iii)

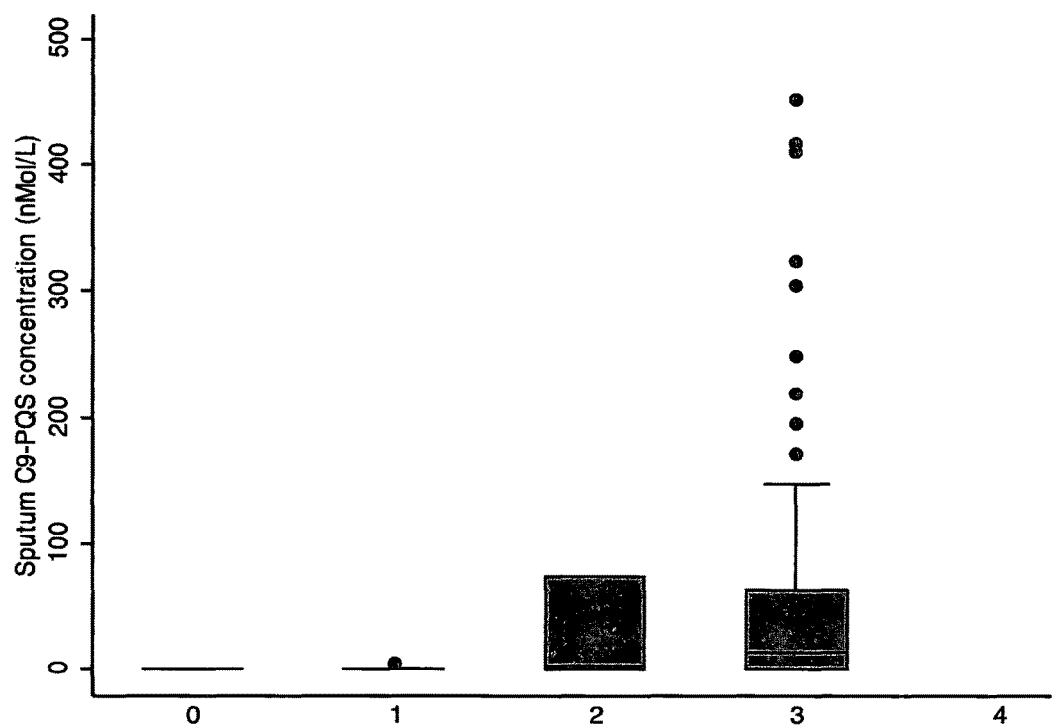
Figure 5 (i)
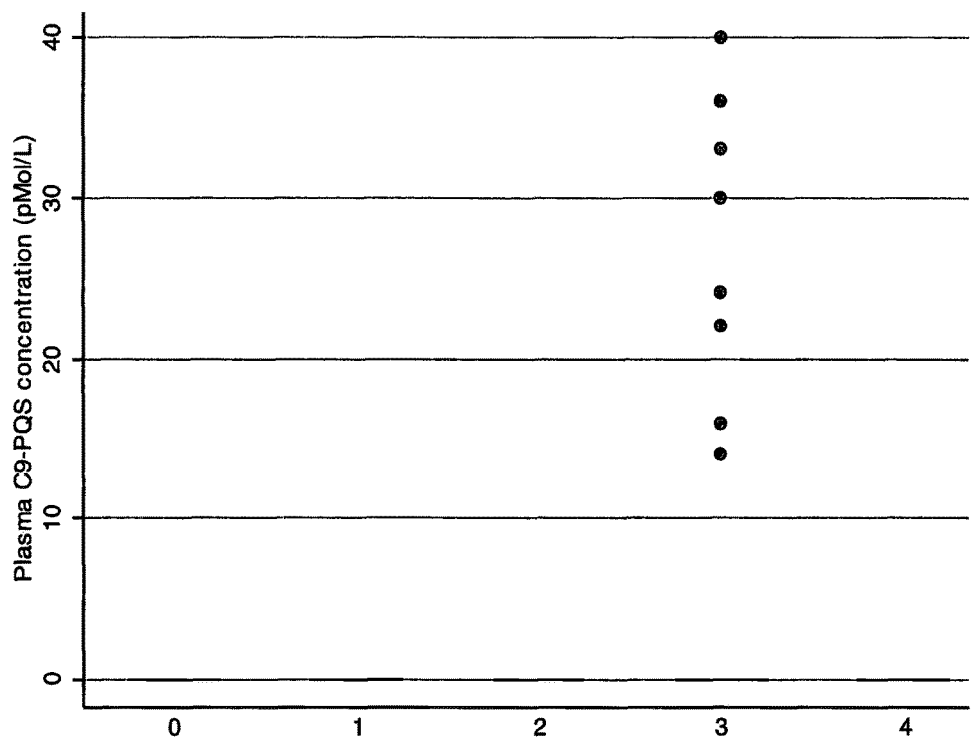
Figure 5 (ii)

Figure 5 (iii)

| QS signal | Density of *P. aeruginosa* (Log₁₀ CFU on PIA/g) | P value |
|---|---|---|
| Sputum | | N=52 |
| HHQ | 0.49 | 0.0002 |
| NHQ | 0.48 | 0.003 |
| HQNO | 0.34 | 0.01 |
| NQNO | 0.31 | 0.03 |
| C7-PQS | 0.41 | 0.003 |
| C9-PQS | 0.25 | 0.08 |
| | | |
| Plasma | | N=48 |
| HHQ | 0.47 | 0.0007 |
| NHQ | 0.30 | 0.04 |
| HQNO | 0.47 | 0.0008 |
| NQNO | 0.34 | 0.02 |
| C7-PQS | 0.36 | 0.01 |
| Urine | | N=51 |
| HHQ | 0.26 | 0.06 |
| NHQ | 0.27 | 0.06 |
| HQNO | 0.29 | 0.04 |
| NQNO | 0.34 | 0.01 |

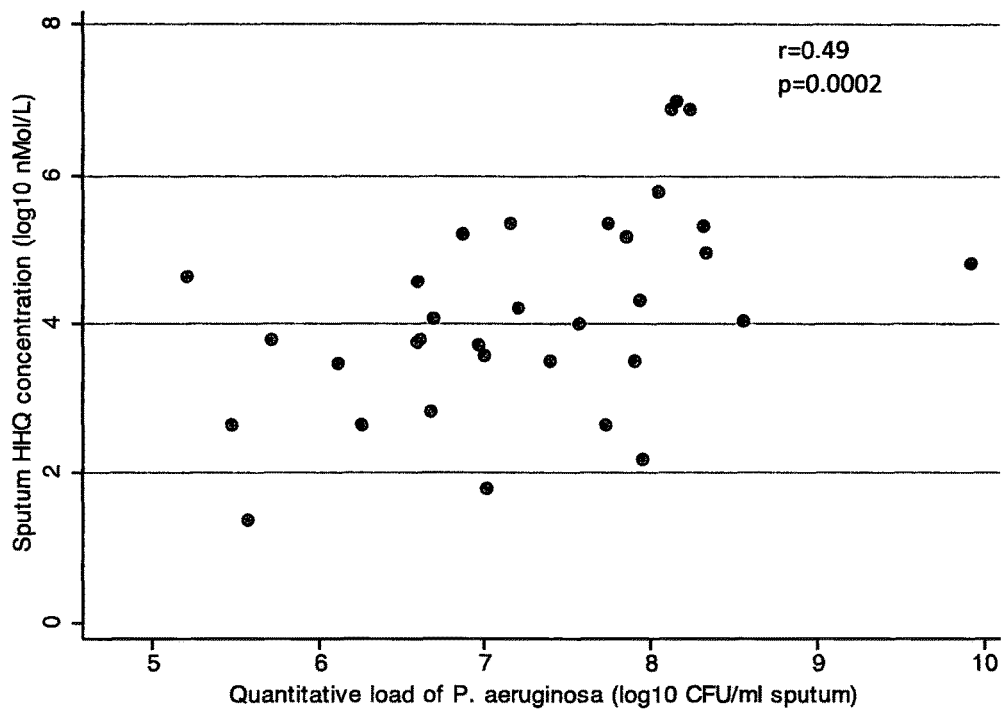
Figure 7 (i)
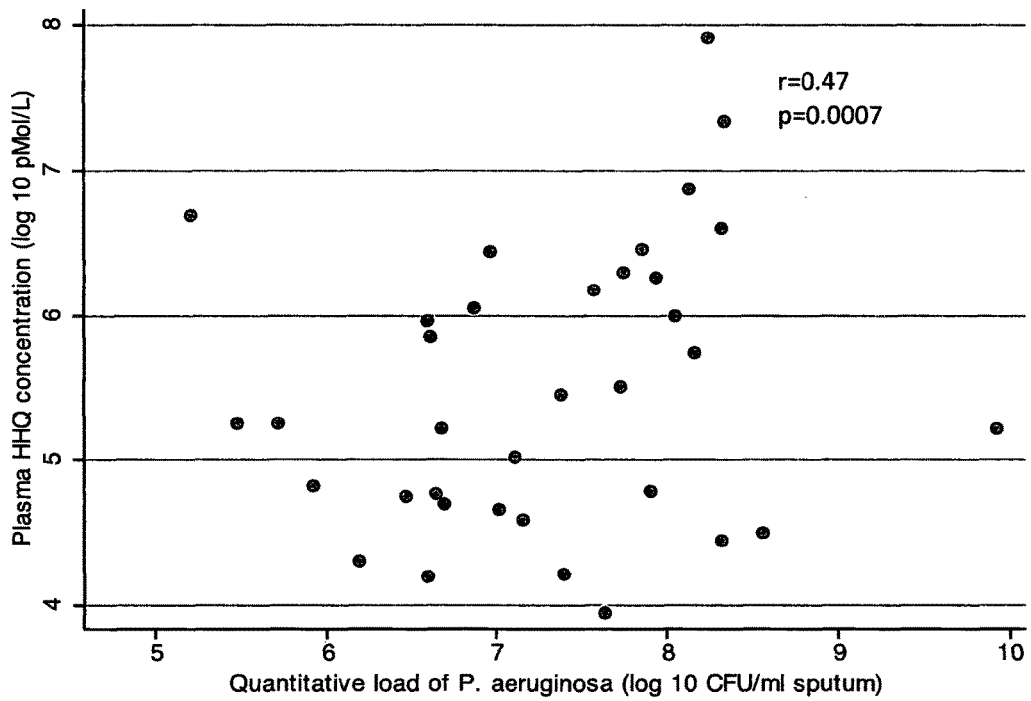
Figure 7 (ii)

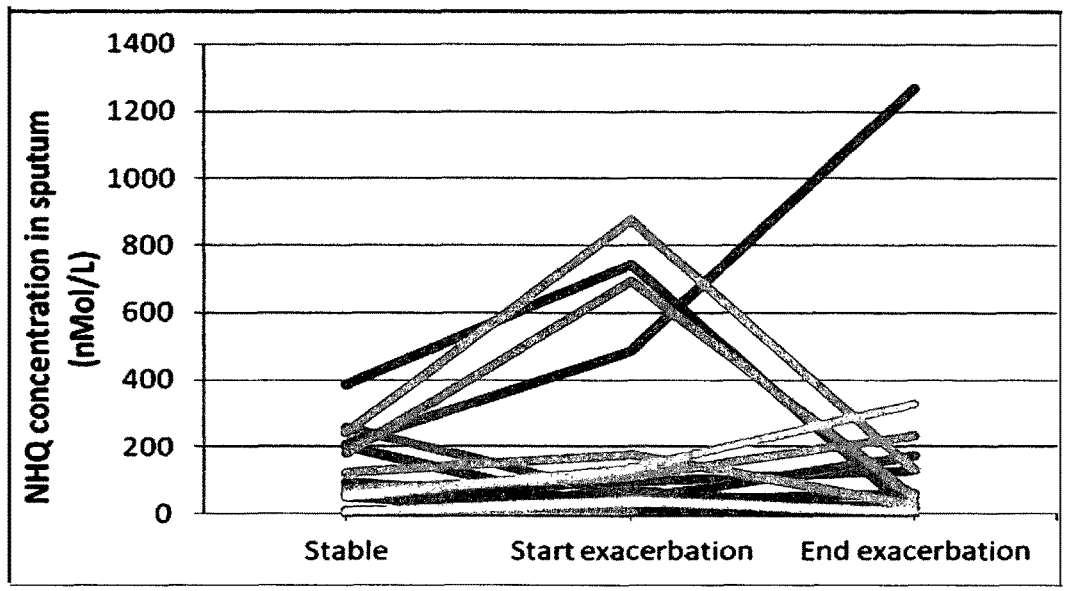
Figure 8 (i)
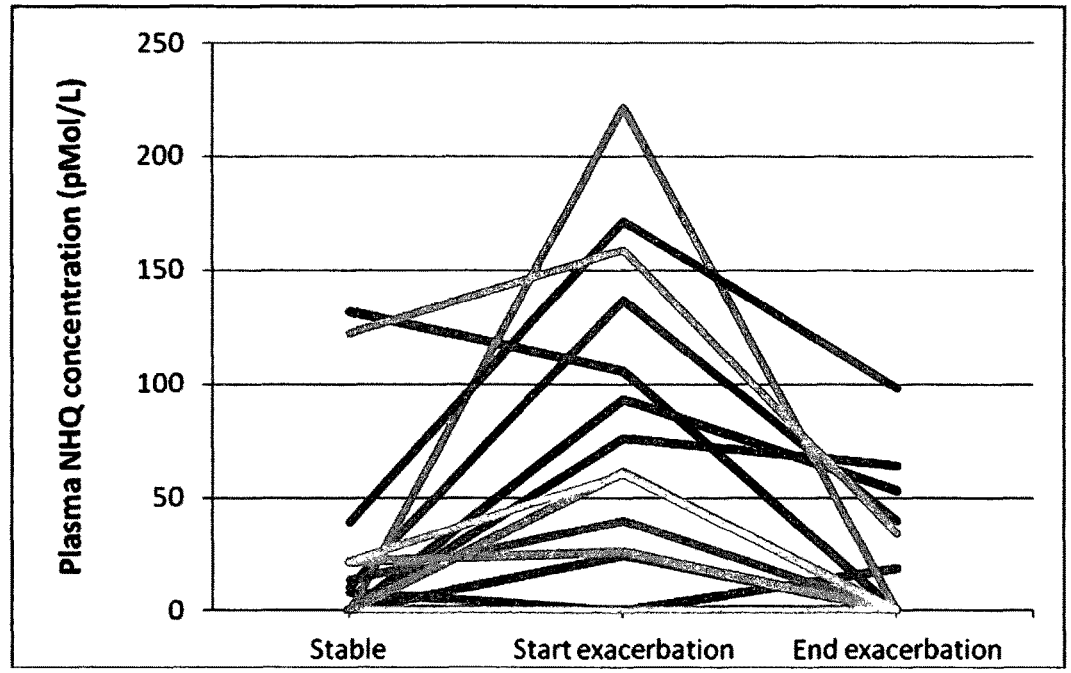
Figure 8 (ii)

Figure 8 (iii)

Figure 9:
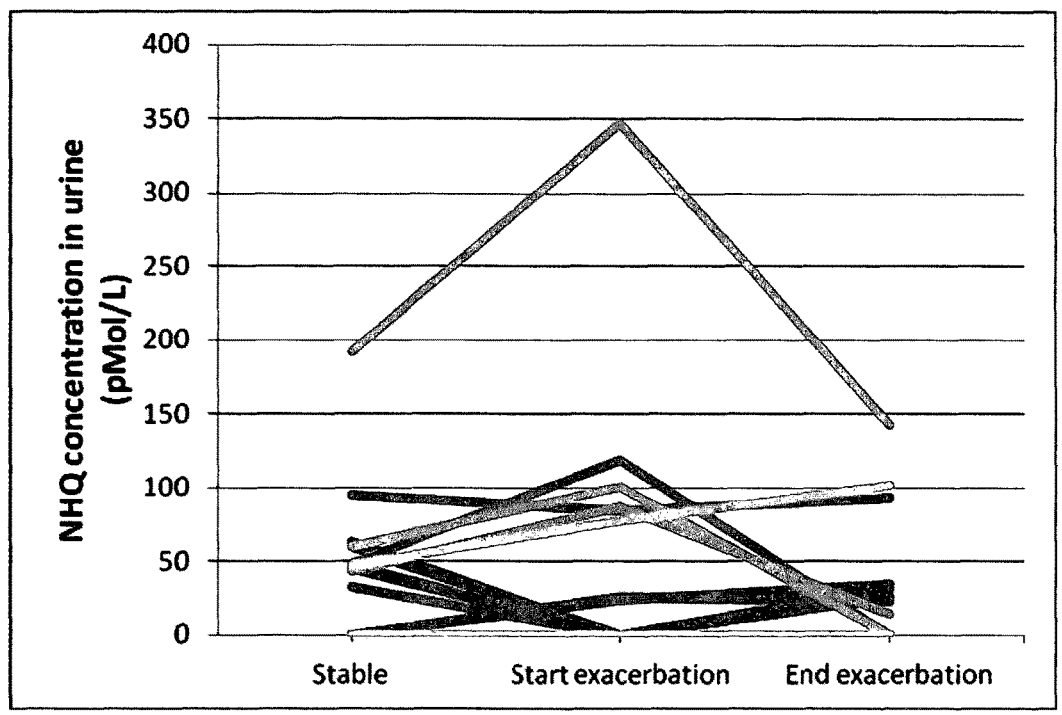
Figure 9:
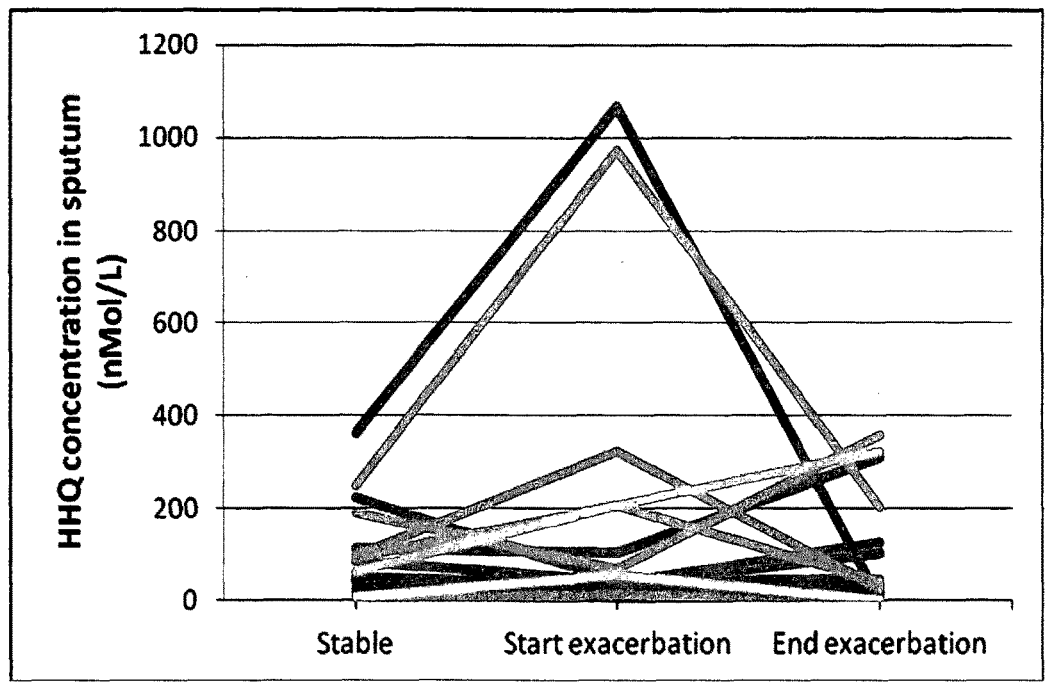

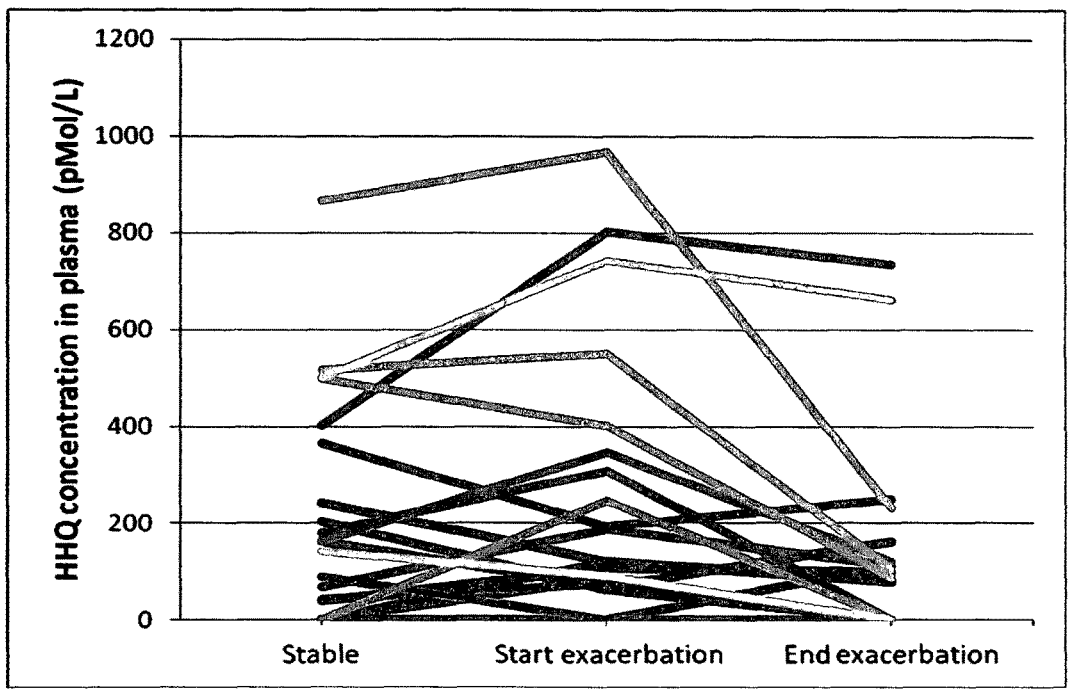
Figure 9 (ii)
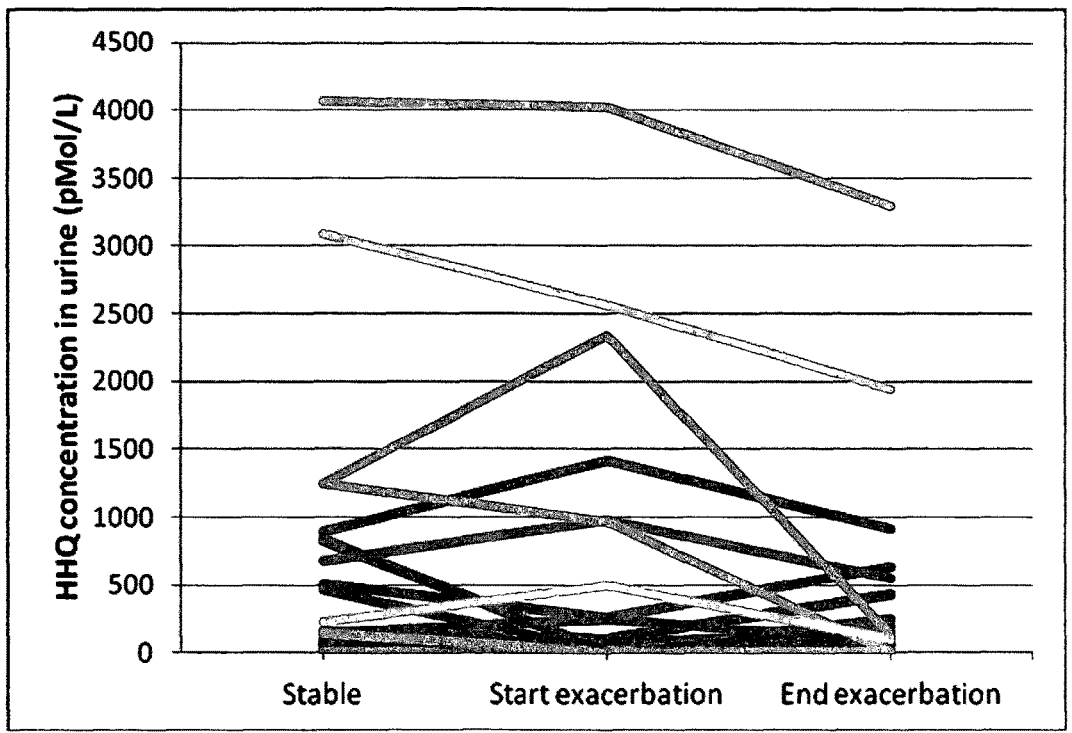
Figure 9 (iii)

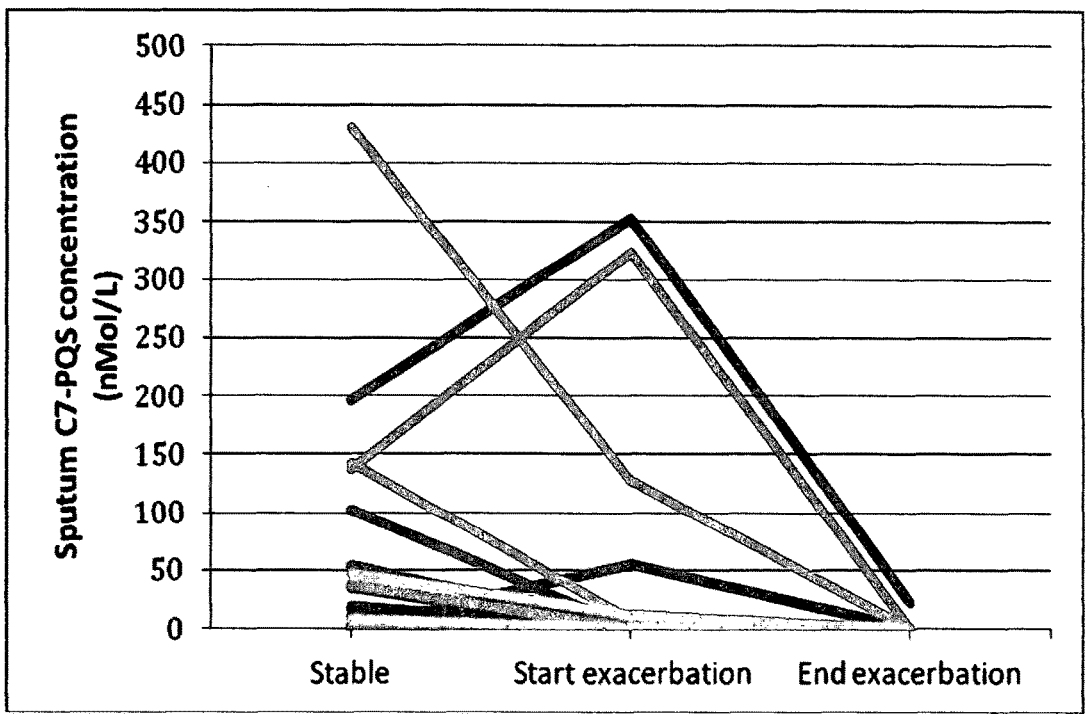
Figure 10 (i)
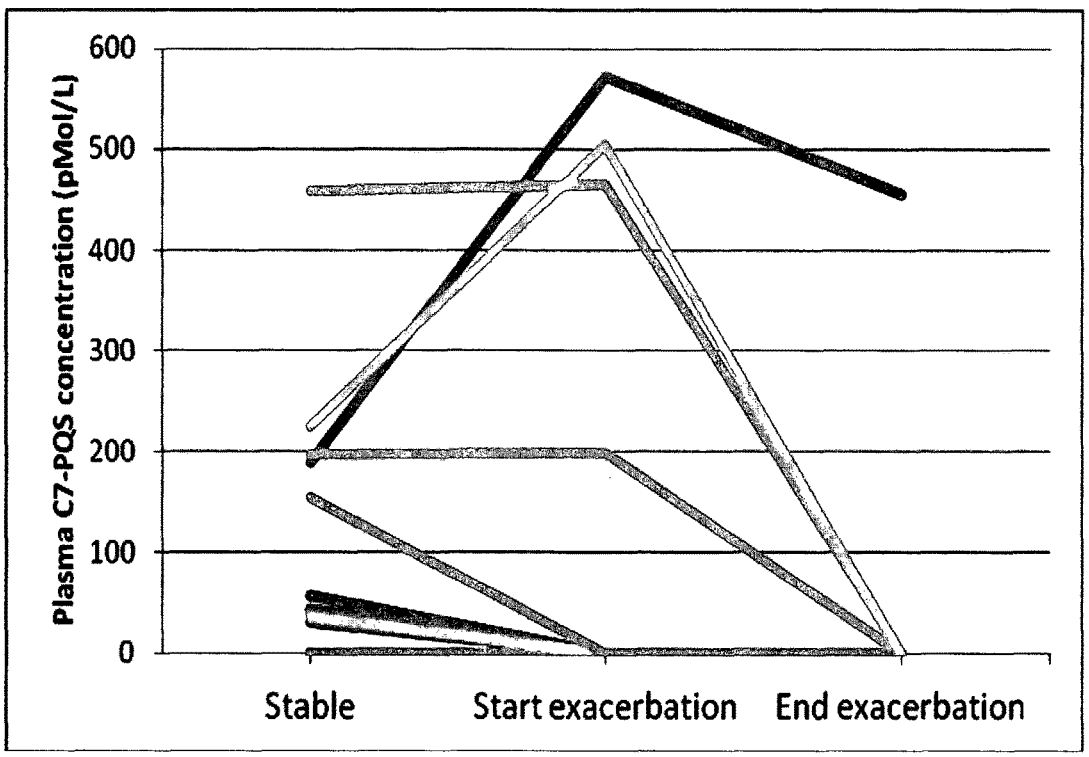
Figure 10 (ii)

A.

B.

C.

| Matrix | Analyte | Concentration (nM) | Intra-day (n=3) | | Inter-day (n=5) | |
|---|---|---|---|---|---|---|
| | | | Accuracy (%) | Precision (CV%) | Accuracy (%) | Precision (CV%) |
| Urine | HHQ | 0.5 | 110.6 | 6.0 | 103.0 | 7.3 |
| | | 4.0 | 102.1 | 3.5 | 103.4 | 11.6 |
| | C7-PQS | 0.5 | 111.6 | 9.5 | 99.8 | 5.5 |
| | | 4.0 | 97.1 | 5.7 | 103.8 | 4.3 |
| | HQNO | 0.5 | 99.0 | 7.9 | 96.9 | 10.4 |
| | | 4.0 | 103.3 | 6.8 | 104.6 | 4.3 |
| Plasma | HHQ | 1.0 | 105.3 | 6.1 | 106.8 | 6.8 |
| | | 8.0 | 101.2 | 8.4 | 104.0 | 5.9 |
| | C7-PQS | 1.0 | 97.7 | 8.0 | 90.7 | 5.4 |
| | | 8.0 | 106.3 | 3.4 | 106.5 | 1.8 |
| | HQNO | 1.0 | 102.5 | 13.0 | 97.9 | 8.4 |
| | | 8.0 | 104.8 | 8.2 | 100.8 | 4.5 |

Figure 13

A.

B.

| Analyte | Concentration | Intra-day (n=3) | | Inter-day (n=3) | |
|---|---|---|---|---|---|
| | | Accuracy | Precision | Accuracy | Precision |
| | (nM) | (%) | (CV%) | (%) | (CV%) |
| HHQ | 75 | 99.6 | 6.2 | 108.3 | 5.3 |
| | 800 | 89.7 | 2.9 | 89.9 | 9.9 |
| C7-PQS | 75 | 89.2 | 18.6 | 107.1 | 9.5 |
| | 800 | 86.3 | 2.1 | 93.9 | 5.2 |
| HQNO | 75 | 95.7 | 20.2 | 100.2 | 17.7 |
| | 800 | 79.8 | 3.9 | 100.4 | 7.0 |

Figure 15

|  | -R | Patient A | Patient B | Patient C | Patient D | Patient E | Patient F |
|---|---|---|---|---|---|---|---|
| Formula I / II  | Saturated | | | | | | |
| | -$C_5H_{11}$ | ✓ | ✓ | ✓ | - | ✓ | - |
| | -$C_6H_{13}$ | ✓ | ✓ | ✓ | - | - | - |
| | -$C_7H_{15}$ | ✓ | ✓ | ✓ | - | ✓ | ✓ |
| | -$C_8H_{17}$ | ✓ | ✓ | ✓ | - | ✓ | ✓ |
| | -$C_9H_{19}$ | ✓ | ✓ | ✓ | - | ✓ | ✓ |
| | -$C_{10}H_{12}$ | ✓ | ✓ | - | - | ✓ | ✓ |
| | -$C_{11}H_{23}$ | ✓ | ✓ | ✓ | ✓ | ✓ | ✓ |
| | -$C_{13}H_{27}$ | ✓ | ✓ | ✓ | - | ✓ | ✓ |
| | Unsaturated | | | | | | |
| | -$C_5H_9$ | - | - | - | - | - | - |
| | -$C_6H_{11}$ | - | - | - | - | - | - |
| | -$C_7H_{13}$ | ✓ | - | - | - | - | ✓ |
| | -$C_8H_{15}$ | ✓ | ✓ | - | - | - | ✓ |
| | -$C_9H_{17}$ | ✓ | ✓ | - | - | - | ✓ |
| | -$C_{10}H_{19}$ | - | - | - | - | - | - |
| | -$C_{11}H_{21}$ | ✓ | ✓ | ✓ | - | ✓ | ✓ |
| | -$C_{12}H_{23}$ | ✓ | ✓ | ✓ | - | ✓ | ✓ |
| | -$C_{13}H_{25}$ | ✓ | ✓ | ✓ | ✓ | ✓ | ✓ |

| | | | | | | | |
|---|---|---|---|---|---|---|---|
| Formula III / IV | Saturated | | | | | | |
| | -C₇H₁₅ | ✓ | - | - | - | - | - |
| | -C₈H₁₇ | - | - | - | - | - | - |
| | -C₉H₁₉ | ✓ | - | - | - | - | - |
| | -C₁₁H₂₃ | ✓ | ✓ | - | - | - | - |
| Formula V / VI | Saturated | | | | | | |
| | -C₅H₁₁ | ✓ | - | - | - | - | ✓ |
| | -C₆H₁₃ | - | - | - | - | - | - |
| | -C₇H₁₅ | ✓ | ✓ | ✓ | - | ✓ | ✓ |
| | -C₈H₁₇ | ✓ | - | - | - | ✓ | - |
| | -C₉H₁₉ | ✓ | ✓ | ✓ | - | ✓ | ✓ |
| | -C₁₀H₁₂ | ✓ | - | - | - | - | - |
| | -C₁₁H₂₃ | ✓ | ✓ | - | - | - | ✓ |
| | Unsaturated | | | | | | |
| | -C₇H₁₃ | ✓ | - | - | - | - | - |
| | -C₈H₁₅ | ✓ | - | - | - | - | - |
| | -C₉H₁₇ | ✓ | ✓ | - | - | - | - |
| | -C₁₀H₁₉ | ✓ | - | - | - | - | - |
| | -C₁₁H₂₁ | ✓ | - | ✓ | - | - | - |
| | -C₁₂H₂₃ | ✓ | - | - | - | - | ✓ |

Figure 16 continued

| | Saturated | | | | | | |
|---|---|---|---|---|---|---|---|
| Formula VII / VIII | -C₅H₁₁ | - | - | - | - | - | - |
| | -C₆H₁₃ | - | - | - | - | - | - |
| | -C₇H₁₅ | - | - | - | - | - | - |
| | -C₈H₁₇ | - | - | - | - | - | - |
| | -C₉H₁₉ | - | - | - | - | - | - |
| | -C₁₁H₂₃ | - | - | - | - | - | - |
| | Unsaturated | | | | | | |
| | -C₅H₉ | ✓ | | ✓ | | ✓ | ✓ |
| | -C₇H₁₃ | ✓ | ✓ | ✓ | ✓ | ✓ | ✓ |
| | -C₉H₁₇ | ✓ | ✓ | ✓ | ✓ | ✓ | ✓ |
| Formula IX / X / XI | N/A | ✓ | ✓ | ✓ | - | - | ✓ |

Figure 16 continued

| | Metabolite | Blood Plasma | Urine |
|---|---|---|---|
| Formula I (HHQ) | Ia | ✓ | ✓ |
| | Ib | ✓ | ✓ |
| | Ic | ✓ | ✓ |
| | Id | - | - |
| | Ie | ✓ | ✓ |
| | If | ✓ | ✓ |
| | Ig | ✓ | ✓ |
| | Ih | ✓ | ✓ |
| Formula III (PQS) | IIIa | - | - |
| | IIIb | - | - |
| | IIIc | - | - |
| | IIId | - | - |
| | IIIe | - | - |
| | IIIf | ✓ | ✓ |
| Formula V (C7-NO) | Va | ✓ | ✓ |
| | Vb | ✓ | ✓ |
| | Vc | ✓ | ✓ |
| | Vd | ✓ | ✓ |
| | Ve | ✓ | ✓ |
| | Vf | ✓ | ✓ |
| | Vg | ✓ | ✓ |
| | Vh | ✓ | ✓ |
| | Vi | - | - |

Figure 17

ALKYL QUINOLONES AS BIOMARKERS OF PSEUDOMONAS AERUGINOSA INFECTION AND USES THEREOF

This application is a 35 U.S.C. § 371 national stage filing of International Application No. PCT/GB2014/051458, filed May 13, 2014, which claims priority of United Kingdom Patent Application No. 1308639.2, filed May 14, 2013. The content of each of the aforementioned applications is incorporated by reference herein in its entirety.

The present invention relates to novel biomarkers for determining the *Pseudomonas aeruginosa* or related organism infection status of a subject, and to uses of the novel biomarkers.

*Pseudomonas aeruginosa* (*P. aeruginosa*) is an opportunistic gram negative bacterium able to infect susceptible individuals with airways diseases such as cystic fibrosis, bronchiectasis and COPD although it can also infect other body parts including wounds and also catheters and prosthetic replacements.

Infection with *P. aeruginosa* was first identified as an important clinical event with regard to cystic fibrosis and bronchiectasis; and is often associated with persistent infection and may be a key factor in accelerating disease progression. By the third decade of life, 80% of cystic fibrosis patients are infected with *P. aeruginosa*, an event associated with an accelerated decline in lung function and subsequent premature death. The first episode of *P. aeruginosa* infection is commonly treated with antibiotic eradication therapy aiming to prevent long-term chronic infection. While eradication of *P. aeruginosa* from patients who have become infected may not be possible in all cases, treatment in the early stages of infection improves the chances of subsequently eliminating the bacterium. To enable this, sensitive diagnostic testing is required to permit early detection of infection before it becomes evident using standard microbiology techniques. Subsequent exacerbations of chest symptoms in those known to be chronically infected with *P. aeruginosa* are treated with appropriate antibiotics, usually by an intravenous route. The total costs of treating cystic fibrosis are large, much of which is due to treating the burden of *P. aeruginosa* in the lungs of patients with cystic fibrosis. The annual cost of caring for a cystic fibrosis patient was estimated as being at least £3600/year in childhood, which would approximate to at least £28 million/year in the UK, although this is probably an underestimate.

Recent epidemiological research has suggested that *P. aeruginosa* may also be an important pathogen with regard to other widespread respiratory diseases such as chronic obstructive pulmonary disease (COPD), with *P. aeruginosa* being implicated in exacerbations in up to 31% of patients with COPD growing *P. aeruginosa* in their sputum and *P. aeruginosa* acquisition being associated with acute exacerbations of disease. This observation has dramatic implications for the clinical management of COPD, a disease which is estimated to annually cost the NHS in the UK approximately £982 million. COPD is common with a prevalence of 7-23% in adults, and conventional management of exacerbations is costly, often involving hospital admission and the use of empirical antibiotics.

At present, the only readily available technique for the diagnosis of *P. aeruginosa* infection in most centres is to use traditional microbiological techniques involving bacterial culture and expectorated sputum. While the use of PCR-based assays has been assessed, these methods currently offer no additional clinical benefit to conventional microbiological diagnostic culture and have the risk of providing false positive results due to the possibility of amplifying small traces of bacterial contamination during the sampling process. The potential of serological measures in diagnosing *P. aeruginosa* infection has been a topic of speculation and research for over 20 years, but to date there is no clear consensus on the clinical role of antibodies to *P. aeruginosa*. Therefore, new diagnostic techniques to diagnose *P. aeruginosa* and the status of the infection caused by this organism are urgently required, to permit appropriate treatment of exacerbations and prevent the accelerated decline in lung function and subsequent clinical deterioration.

According to a first aspect the invention provides a method of determining the *P. aeruginosa* or related species infection status of a subject comprising:
  (a) providing a sample of material obtained from the subject;
  (b) determining the level of one or more alkyl quinolones or metabolites thereof produced by *P. aeruginosa* or a related species in the sample Preferable the level of at least 1, 2, 3, 4, 5, 6, 7, 8, 9, 10 or more, 20 or more, 30 or more, 40 or more, 50 or more, 60 or more, 70 or more, 80 or more, 90 or more, or 100 or more alkyl quinolones or metabolites thereof are determined in the method of the invention.

Reference herein to an alkyl quinolone produced by *P. aeruginosa* or a related species is intended to include one or more of the compounds described below with reference to Formula I to Formula XI:

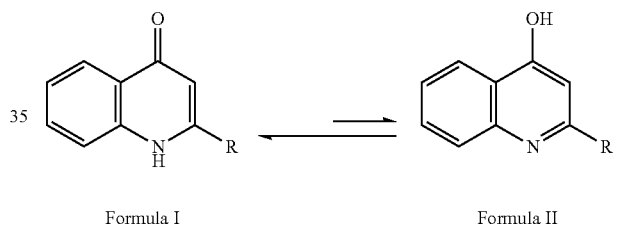

Formula I                Formula II

Wherein in Formula I and Formula II R may be a saturated chain selected from the group comprising: n-$C_5H_{11}$, n-$C_6H_{13}$, n-$C_7H_{15}$, n-$C_8H_{17}$, n-$C_9H_{19}$, n-$C_{10}H_{21}$, n-$C_{11}H_{23}$, n-$C_{12}H_{25}$ and n-$C_{13}H_{27}$; or R may be an unsaturated chain selected from the group comprising: n-$C_5H_9$, n-$C_6H_{11}$, n-$C_7H_{13}$, n-$C_8H_{15}$, n-$C_9H_{17}$, n-$C_{10}H_{19}$, n-$C_{11}H_{21}$, n-$C_{12}H_{23}$ and n-$C_{13}H_{25}$. Preferably in Formula I and Formula II R may be a saturated chain selected from the group comprising: n-$C_5H_{11}$, n-$C_6H_{13}$, n-$C_7H_{15}$, n-$C_8H_{17}$, n-$C_9H_{19}$, n-$C_{10}H_{21}$, n-$C_{11}H_{23}$ and n-$C_{13}H_{27}$; or R may be an unsaturated chain selected from the group comprising: n-$C_5H_9$, n-$C_6H_{11}$, n-$C_7H_{13}$, n-$C_8H_{15}$, n-$C_9H_{17}$, n-$C_{10}H_{19}$, n-$C_{11}H_{21}$, n-$C_{12}H_{23}$ and n-$C_{13}H_{25}$.

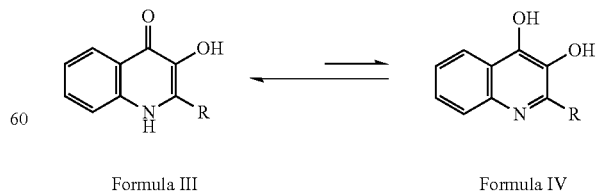

Formula III              Formula IV

Wherein in Formula III and Formula IV R may be a saturated chain selected from the group comprising: n-$C_5H_{11}$, n-$C_6H_{13}$, n-$C_7H_{15}$, n-$C_8H_{17}$, n-$C_9H_{19}$, n-$C_{10}H_{21}$, n-$C_{11}H_{23}$, n-$C_{12}H_{25}$ and n-$C_{13}H_{27}$; or R may be an unsaturated chain selected from the group comprising: n-$C_5H_9$, n-$C_6H_{11}$, n-$C_7H_{13}$, n-$C_8H_{15}$, n-$C_9H_{17}$, n-$C_{10}H_{19}$, n-$C_{11}H_{21}$, n-$C_{12}H_{23}$ and n-$C_{13}H_{25}$. Preferably in Formula III and Formula IV R may be a saturated chain selected from the group comprising: n-$C_7H_{15}$, n-$C_8H_{17}$, n-$C_9H_{19}$ and n-$C_{11}H_{23}$.

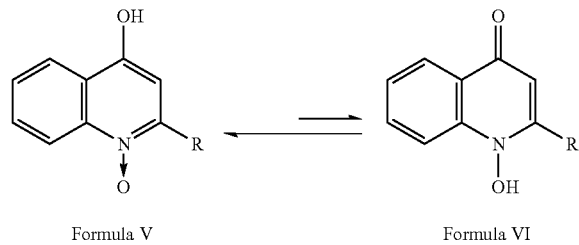

Formula V    Formula VI

Wherein in Formula VII and Formula VIII R may be a saturated chain selected from the group comprising: n-$C_5H_{11}$, n-$C_6H_{13}$, n-$C_7H_{15}$, n-$C_8H_{17}$, n-$C_9H_{19}$, n-$C_{10}H_{21}$, n-$C_{11}H_{23}$, n-$C_{12}H_{25}$ and n-$C_{13}H_{27}$; or R may be an unsaturated chain selected from the group comprising: n-$C_5H_9$, n-$C_6H_{11}$, n-$C_7H_{13}$, n-$C_8H_{15}$, n-$C_9H_{17}$, n-$C_{10}H_{19}$, n-$C_{11}H_{21}$, n-$C_{12}H_{23}$ and n-$C_{13}H_{25}$. Preferably in Formula VII and Formula VIII R may be a saturated chain selected from the group comprising n-$C_5H_{11}$, n-$C_6H_{13}$, n-$C_7H_{15}$, n-$C_8H_{17}$, n-$C_9H_{19}$ and n-$C_{11}H_{23}$; or R may be an unsaturated chain selected from the group comprising: n-$C_5H_9$, n-$C_7H_{13}$ and n-$C_9H_{17}$.

In a compound of Formula I, II, V, VI, VII or VIII in which the side chain (R group) is unsaturated the double bond may be between α and β carbons of the chain, and may be in a cis- or trans-configuration.

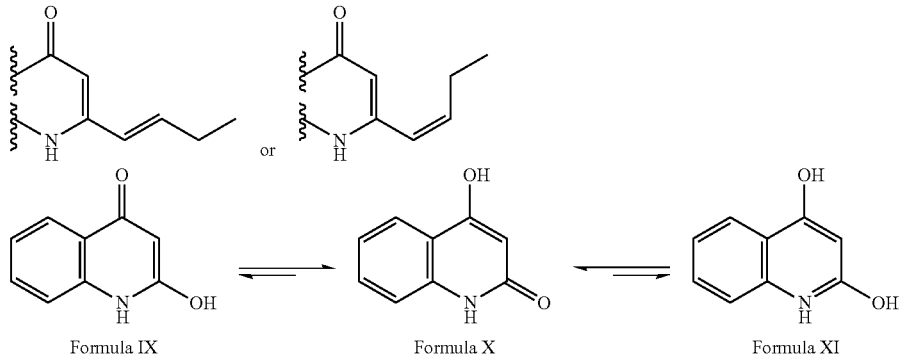

Formula IX    Formula X    Formula XI

Wherein in Formula V and Formula VI R may be a saturated chain selected from the group comprising: n-$C_5H_{11}$, n-$C_6H_{13}$, n-$C_7H_{15}$, n-$C_8H_{17}$, n-$C_9H_{19}$, n-$C_{10}H_{21}$, n-$C_{11}H_{23}$, n-$C_{12}H_{25}$ and n-$C_{13}H_{27}$; or R may be an unsaturated chain selected from the group comprising: n-$C_5H_9$, n-$C_6H_{11}$, n-$C_7H_{13}$, n-$C_8H_{15}$, n-$C_9H_{17}$, n-$C_{10}H_{19}$, n-$C_{11}H_{21}$, n-$C_{12}H_{23}$ and n-$C_{13}H_{25}$. Preferably in Formula V and Formula VI R may be a saturated chain selected from the group comprising n-$C_5H_{11}$, n-$C_6H_{13}$, n-$C_7H_{15}$, n-$C_8H_{17}$, n-$C_9H_{19}$, n-$C_{10}H_{21}$ and n-$C_{11}H_{23}$; or R may be an unsaturated chain selected from the group comprising: n-$C_7H_{13}$, n-$C_8H_{15}$, n-$C_9H_{17}$, n-$C_{10}H_{19}$, n-$C_{11}H_{21}$, and n-$C_{12}H_{23}$.

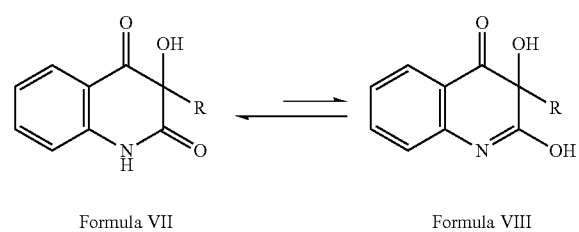

Formula VII    Formula VIII

Preferably the one or more alkyl quinolones in the method of the invention are selected from group comprising compounds of Formula I or Formula II wherein the R group is n-$C_7H_{15}$, n-$C_9H_{19}$, or n-$C_{11}H_{23}$; compounds of Formula III and Formula IV wherein the R group is n-$C_7H_{15}$, n-$C_9H_{19}$ or n-$C_{11}H_{23}$; and compounds of Formula V or Formula VI wherein the R group is n-$C_7H_{15}$ or n-$C_9H_{19}$.

More preferably the one or more alkyl quinolones in the method of the invention are selected from group comprising compounds of compounds of Formula I wherein the R group is n-$C_7H_{15}$, n-$C_9H_{19}$, or n-$C_{11}H_{23}$; Formula III wherein the R group is n-$C_7H_{15}$, n-$C_9H_{19}$ or n-$C_{11}H_{23}$; and compounds of Formula V wherein the R group is n-$C_7H_{15}$ or n-$C_9H_{19}$.

In a preferred embodiment the one or more alkyl quinolones are selected from the group comprising compounds of Formula I, II, III, IV, V and VI wherein the R group is n-$C_7H_{15}$.

In a further embodiment the one or more alkyl quinolones are selected from the group comprising compounds of Formula I, III and V wherein the R group is n-$C_7H_{15}$.

Alkyl quinolones can undergo intramolecular rearrangements to give tautomeric forms of the same compound, for example Formula I and Formula II are two tautomeric forms of the same compound, Formula III and Formula IV are two tautomeric forms of the same compound, Formula V and Formula VI are two tautomeric forms of the same compound, Formula VII and Formula VIII are two tautomeric forms of the same compound, and Formula IX, Formula X and Formula X1 are three tautomeric forms of the same compound. The predominance of one tautomeric form over the other is thought to be largely determined by the pH. At physiological pH, the compounds of Formula I, III, V, VII and X are the predominant forms (as indicated by the arrows).

Reference herein to metabolites of the alkyl quinolones is intended to encompass all metabolites of the alkyl quinolones that arise due to degradation and/or modification of the compounds in a subject. In particular, the compounds are often modified and/or degraded in order to facilitate excretion.

Metabolites of a compound of Formula I, referred to in the scheme below as Formula 1a in which the R group is n-$C_7H_{15}$, are depicted below as Formulae Ib to Ih. The compound of Formula I depicted as Formula 1a may also be referred to as HHQ—2-heptyl-4(1H)-quinolone. The skilled man will appreciate that n-$C_7H_{15}$ could be substituted with any other suggested R group and corresponding metabolites may form. The skilled person will also appreciate that comparable metabolites would form if the starting compound was of Formula II (a tautomeric form of the compound of Formula I depicted in the figure as Formula 1aa).

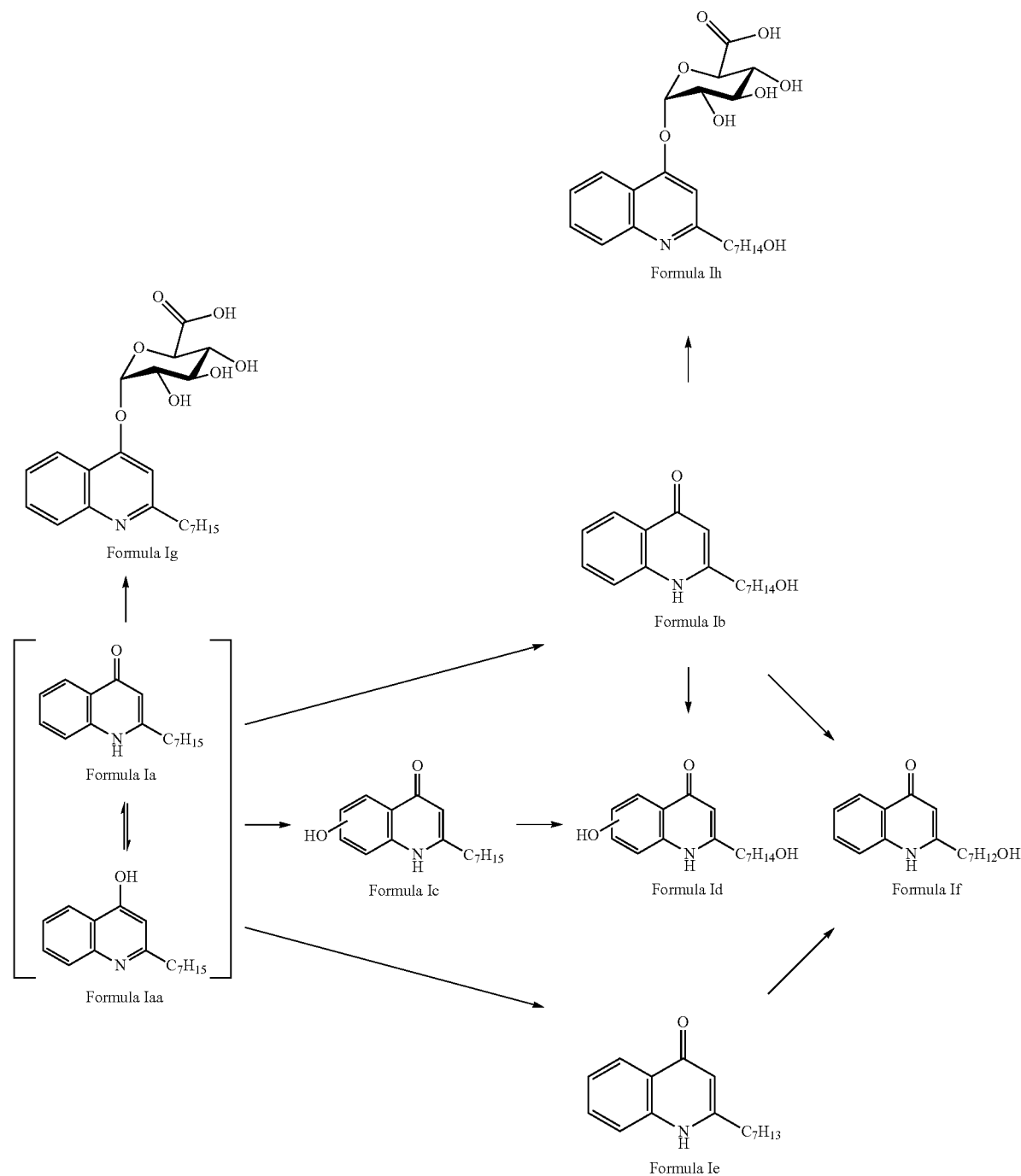

Metabolites of a compound of Formula III, referred to in the scheme below as Formula IIIa in which the R group is n-$C_7H_{15}$, are depicted below as Formulae IIIb-IIIf. The compound of Formula IIIa depicted may also be referred to as C7-PQS—2-heptyl-3-hydroxy-4(1H)-quinolone. The skilled man will appreciate that n-$C_7H_{15}$ could be substituted with any other suggested R group and corresponding metabolites may form. The skilled person will also appreciate that comparable metabolites would form if the starting compound was of Formula IV (a tautomeric form of the compound of Formula III).

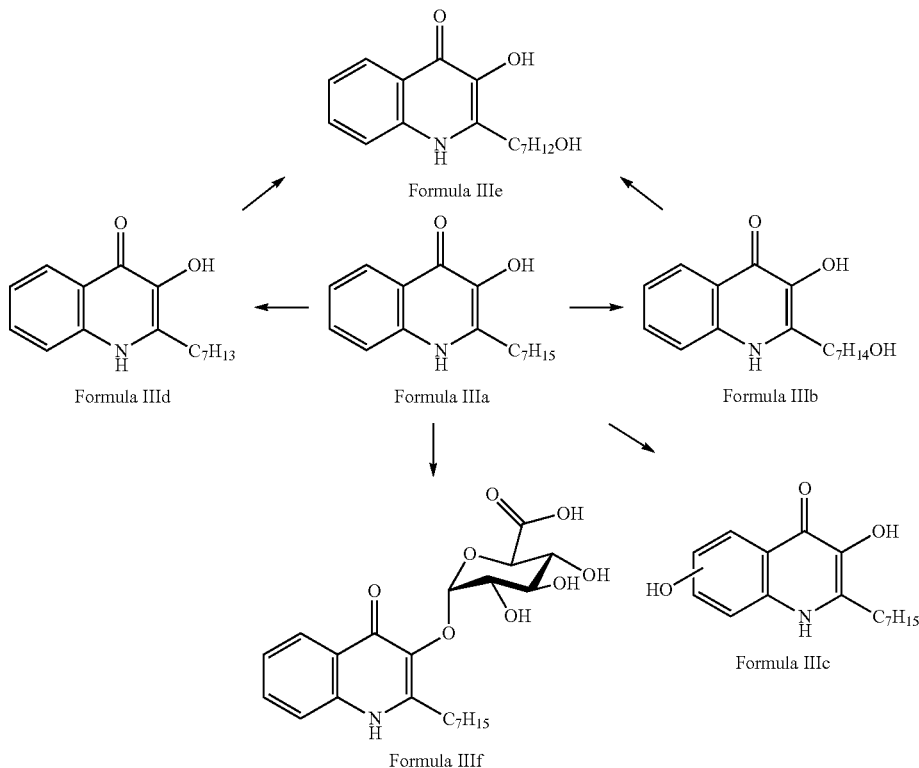

Metabolites of a compounds of Formula V, referred to in the scheme below as Formula Va in which the R group is n-$C_7H_{15}$, are depicted below as Formulae Vb-Vi. The compound of Formula Va depicted is HQNO—2-heptyl-4-hydroxyquinoline N-oxide. The skilled man will appreciate that n-$C_7H_{15}$ could be substituted with any other suggested R group and corresponding metabolites may form. The skilled person will also appreciate that comparable metabolites would form if the starting compound was of Formula VI (a tautomeric form of the compound of Formula V).

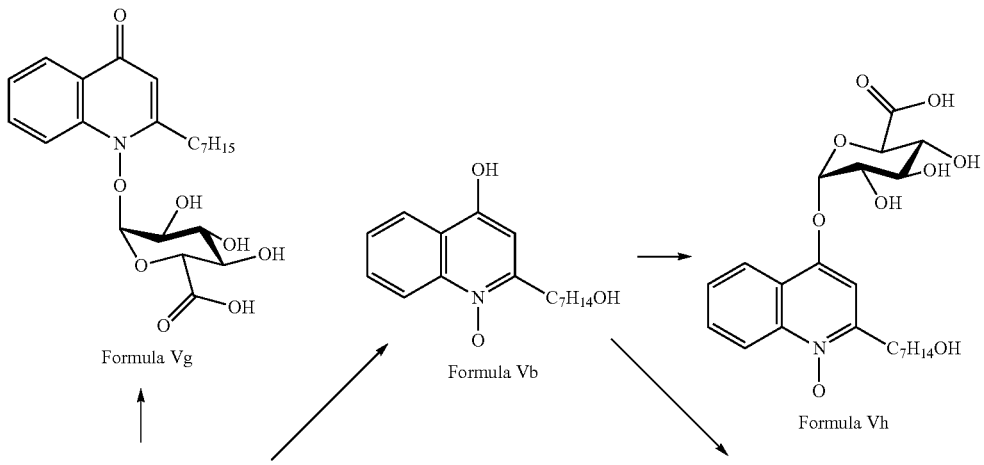

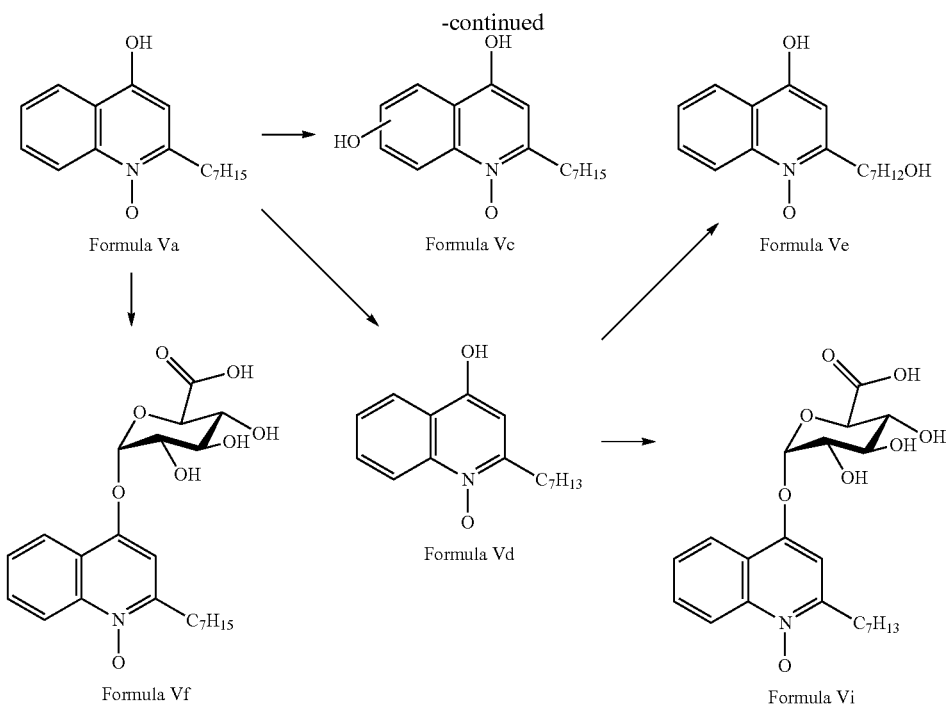

Formula Va
Formula Vc
Formula Ve
Formula Vf
Formula Vd
Formula Vi

Compounds of Formula VII, VIII, IX and X may form metabolites similar to those formed for compounds I, II, III, IV, V and VI, due to the similar molecular structure and positioning of functional groups. Such metabolites would be easily predicted and identified by the skilled person.

Species related to *P. aeruginosa* include closely phylogenetically related bacteria such as *Burkholderia* spp. Closely related *Burkholderia* spp may include the *Burkholderia cenocepacia* complex, which are also major causes of respiratory infections in cystic fibrosis and *Burkholderia pseudomallei*, the causative agent of the tropical disease melioidosis.

Infection status includes any distinguishable manifestation of infection by *P. aeruginosa* or a related species. For example infection status includes, without limitation, the presence or absence of infection, the level of infection, the progression of an infection, and the effectiveness or response of a subject to a particular treatment for infection.

Preferably the method of the invention is able to diagnose infection at levels below that which would be needed to detect infection by standard microbiological techniques.

The method of the invention may, for example, be used for one or more of the following; to diagnose whether or not a subject has *P. aeruginosa*, or related species, infection; to quantify the infectious load of an infection by *P. aeruginosa*, or a related species, in a subject; to advise on the prognosis for a subject with *P. aeruginosa*, or a related species, infection including the onset of an exacerbation; and to monitor effectiveness or response of a subject to a particular treatment for infection by *P. aeruginosa*, or a related species.

The sample of material may be a sample of sputum, saliva, blood, wound exudate, urine, faeces, peritoneal fluid or any sample from the upper or lower respiratory tract, including samples obtained during bronchoalveolar lavage. A sample of blood may be whole blood, blood plasma or blood serum.

Preferably the sample is a sample of blood or urine. These samples have the advantage that they are readily obtainable and tend to more homogenous in nature than other sample types. The finding of alkyl quinolones and metabolites thereof in blood and urine, particularly at detectable levels, was surprising as they are compounds of bacterial origin, non-natural to humans. No data exists in the literature to suggest that they have been detected before in blood and urine, and in the experiments reported herein alkyl quinolones and their metabolites were not detectable in the negative controls (samples from healthy patients with no respiratory history and no previous *P. aeruginosa* infection).

In an embodiment, preferably the sample is not a sputum sample. Sputum samples can be difficult or uncomfortable to obtain, and sometimes require the intervention of specialist medical professionals. Sputum samples are also often not homogeneous and therefore are difficult to obtain quantitative data from.

The level of one or more alkyl quinolones or metabolites thereof produced by *P. aeruginosa* or a related species in a sample may be determined by any suitable method. Such methods include mass spectrometry, immunoassays and biosensors. The biosensor may be a genetically engineered bacterium which responds to a specific molecule by, for example, changing colour or emitting light or fluorescence.

Preferably the method of the invention does not include the step of obtaining the sample.

The method of the invention may include a further step of comparing the determined value of one or more alkyl quinolones or metabolites thereof in a sample with a reference value.

The reference value may be the value for the same one or more alkyl quinolones or metabolites thereof in a sample, preferably a same sample type, from an individual who is known to have or not to have an infection with *P. aeruginosa*, or a related species. Alternatively, or additionally, the reference value may be the level of one or more alkyl quinolones or metabolites thereof in a sample taken previously from the same subject, for example, prior to or during the course of a particular treatment. Preferably the reference sample is a sample of the same type, for example, both samples may be blood samples. In this way the level of one or more alkyl quinolones or metabolites thereof may be used to monitor the progression of an infection in a subject, and/or to monitor the efficacy of a particular treatment in a subject. For example a reduction in the level of one or more alkyl quinolones or metabolites thereof in response to treatment may be indicative that the treatment is having an effect to reduce the level of infection.

Preferably the method of the invention is carried out in vitro.

The subject may be a mammal, and is preferably a human, but may alternatively be a monkey, ape, cat, dog, cow, horse, rabbit or rodent.

According to another aspect of the invention there is provided a kit for use in determining the *P. aeruginosa*, or a related species, infection status in a subject comprising at least one agent for determining the level of one or more alkyl quinolones or metabolites thereof in a sample from a subject.

The agent may be an antibody or a biosensor.

According to a further aspect, the invention provides the use of the determination of the level of one or more alkyl quinolones or metabolites thereof as a means to determine the *P. aeruginosa*, or a related species, infection status in a subject.

According to yet another aspect, the invention provides an alkyl quinolone or metabolite thereof from *P. aeruginosa* or a related species for use as biomarker for infection by *P. aeruginosa* or a related species.

The use of one or more alkyl quinolones or metabolites thereof from *P. aeruginosa* or a related species as a biomarker for infection by *P. aeruginosa* or a related species has many applications positively impacting on clinical care. It permits both the regular screening of susceptible populations and also the testing of all individuals who are suspected of *P. aeruginosa* infection (including those who are not able to produce a sputum sample), and thus enables more timely eradication treatment for initial infection, possibly preventing chronic infection. It also permits a quantitative assessment of the efficacy of antibiotic therapy for the treatment of infective exacerbations, resulting in interventions that are customised to the response of the individual patient. It also provides a tool for widespread use in epidemiological studies, an important consideration as it becomes evident that *P. aeruginosa* infection is more prevalent than was originally appreciated. Finally, a new biomarker for infection with *P. aeruginosa* provides an outcome measure that can be used in the assessment of new anti-pseudomonal antibiotics in the early stages of development, permitting more efficient and rapid assessment of promising agents.

According to another aspect the invention provides an antibody or a biosensor capable of detecting the presence of one or more alkyl quinolones or metabolites thereof from *P. aeruginosa* or a related species in a sample from a subject.

The skilled man will appreciate that preferred features of any one embodiment and/or aspect of the invention may be applied to all other embodiments or aspects of the invention.

Figure 1:
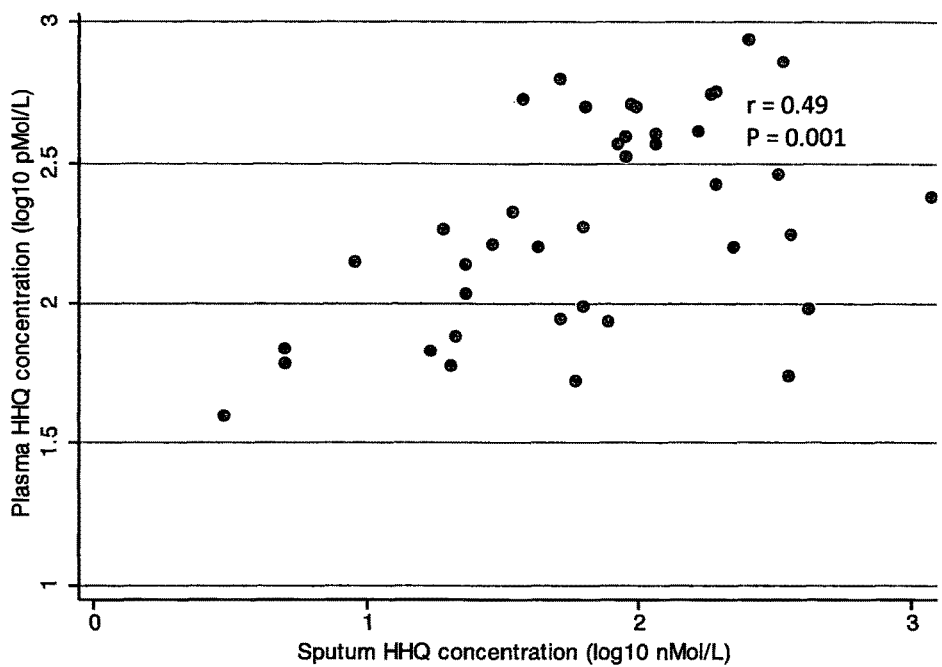

The present invention will be further described in more detail, by way of example only, with reference to the following figures in which:

FIG. 1—illustrates that HHQ can be detected in the plasma of clinically stable CF patients with chronic pulmonary *P. aeruginosa* infection and that plasma concentrations of HHQ (2-heptyl-4-hydroxyquinoline) correlate with sputum levels. More specifically, FIG. 1 illustrates the cross-sectional association between HHQ signal concentration measured in spontaneous sputum and plasma samples from 40 clinically stable CF patients with chronic infection with *P. aeruginosa* with signal levels above the lower limit of detection in each media measured by LCMS/MS (Spearman's correlation coefficient: r=0.49; p=0.001).

Figure 2:
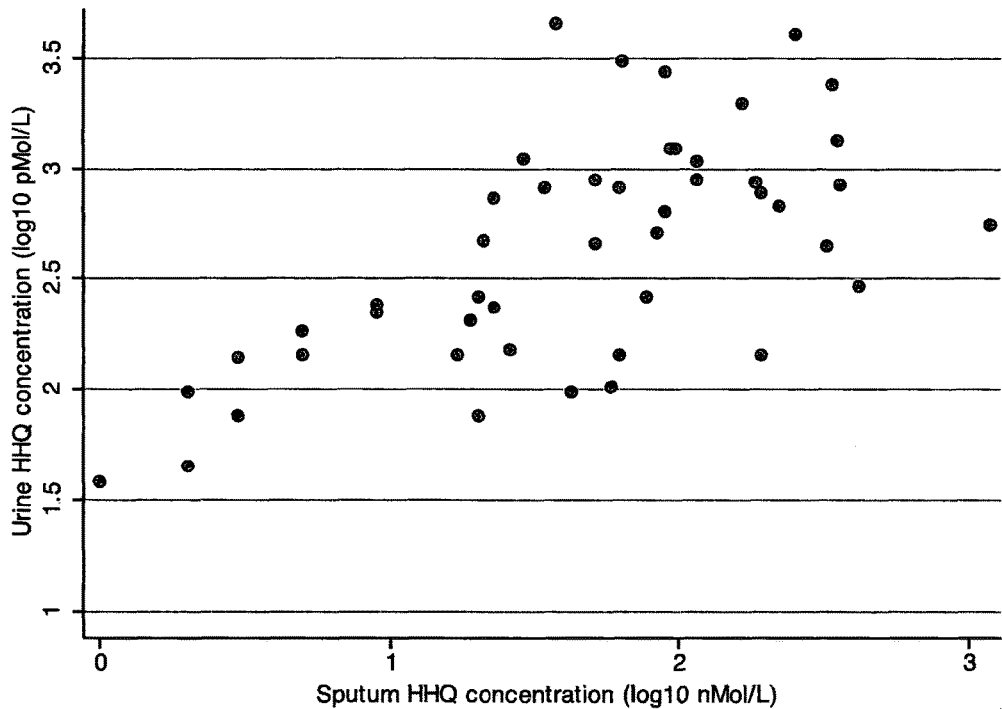

FIG. 2—illustrates that HHQ can be detected in urine samples from clinically stable CF patients with chronic pulmonary *P. aeruginosa* infection and that urinary concentrations of HHQ correlate with sputum levels. More specifically, FIG. 2 illustrates the cross-sectional association between HHQ concentration in spontaneous sputum and urine samples from 47 clinically stable CF patients with chronic infection with *P. aeruginosa* with signal levels above the lower limit of threshold measured by LCMS/MS (Spearman's correlation coefficient: r=0.63; p<0.0001).

FIG. 3—illustrates the results of LCMS/MS analysis of sputum, plasma and urine samples from 58 CF patients with chronic *P. aeruginosa* infection at the start of a pulmonary exacerbation. This demonstrates that plasma and urinary concentrations of HHQ, 2-nonyl-4-hydroxyquinoline (NHQ), HQNO and 2-nonyl-4-hydroxyquinoline N-oxide (NQNO) correlate with sputum levels.

FIG. 4—illustrates that C7-PQS can be detected in sputum, plasma and urine from clinically stable CF patients with chronic pulmonary *P. aeruginosa* infection, but is not detectable above threshold levels for CF patients without pulmonary *P. aeruginosa* infection or in negative healthy controls. More specifically FIG. 4 illustrates the cross-sectional LCMS/MS signal concentrations of C7-PQS detected in (i) sputum, (ii) plasma, (iii) urine of 176 clinically stable CF patients and 22 healthy controls. CF patients are categorised depending on previous hospital microbiological laboratory results as follows: Group 0—CF patients who have never isolated *P. aeruginosa* from the respiratory tract. Group 1—CF patients who have previously isolated *P. aeruginosa* from the respiratory tract but have been free of infection in the last 12 months. Group 2—CF patients who have had less than 50% of respiratory cultures isolate *P. aeruginosa* in the last 12 months. Group 3—CF patients who have had greater than 50% of respiratory cultures in the last 12 months isolate *P. aeruginosa*. Group 4—healthy controls with no respiratory disease and no previous *P. aeruginosa* infection. N=number of participants with data available for analysis. In Figure (i) Group 0 N=4; in Group 1 N=5; in Group 2 N=3; and in Group 3 N=75. In Figure (ii) in Group 0 N=22; in Group 1 N=42; in Group 2 N=23; in Group 3 N=85 and in Group 4 N=22. In Figure (iii) in Group 0 N=22; in Group 1 N=43; in Group 2 N=22; in Group 3 N=87 and in Group 4 N=19.

FIG. 5—illustrates that 2-nonyl-3-hydroxy-4(1H)-quinolone (C9-PQS) can be detected in sputum, plasma and urine from clinically stable CF patients with chronic pulmonary *P. aeruginosa* infection. It also demonstrates that C9-PQS may be detected in biological fluids from patients with intermittent *P. aeruginosa* infection, suggesting it may be a biomarker for early infection. More specifically, FIG. 5 illustrates the cross-sectional LCMS/MS signal concentrations of C9-PQS detected in (i) sputum, (ii) plasma and (iii) urine of 176 clinically stable CF patients and 22 healthy controls. Group 0—CF patients who have never isolated *P. aeruginosa* from the respiratory tract. Group 1—CF patients who have previously isolated *P. aeruginosa* from the respiratory tract but have been free of infection in the last 12 months. Group 2—CF patients who have had less than 50% of respiratory cultures isolate *P. aeruginosa* in the last 12 months. Group 3—CF patients who have had greater than 50% of respiratory cultures in the last 12 months isolate *P. aeruginosa*. Group 4—healthy controls with no respiratory disease and no previous P. aeruginosa infection. N=number of participants with data available for analysis. In Figure (i) in Group 0 N=4; in Group 1 N=5; in Group 2 N=3; and in Group 3N=75. In Figure (ii) in Group 0 N=22; in Group 1 N=42; in Group 2 N=23; in Group 3 N=85 and in Group 4 N=22. In Figure (iii) in Group 0 N=22; in Group 1 N=43; in Group 2 N=22; in Group 3 N=87 and in Group 4 N=19.

Figure 6:
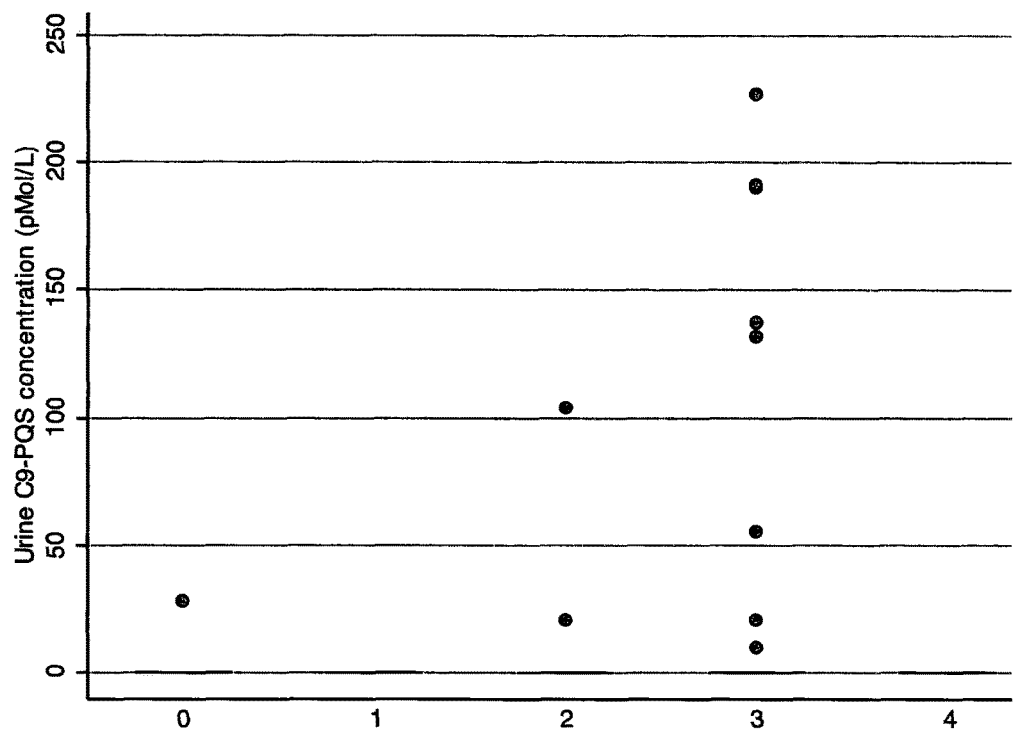

FIG. 6—demonstrates that alkyl quinolone concentrations in the sputum, plasma and urine correlate with quantitative bacterial load of P. aeruginosa measured using traditional culture techniques in CF patients with chronic P. aeruginosa infection at the start of a pulmonary exacerbation. Values are Spearman's correlation coefficients with corresponding p values. The following abbreviations are used in FIG. 6—CFU=colony forming units; PIA=Pseudomonas isolation agar; HHQ=2-heptyl-4-hydroxyquinoline; HHQ=2-nonyl-4-hydroxyquinoline; HQNO=2-heptyl-4-hydroxyquinoline-N-oxide: NQNO=2-nonyl-4-hydroxyquinoline-N-oxide; C7-PQS=2-heptyl-3-hydroxy-4(1H)-quinolone; and N=number of patients.

FIG. 7—illustrates the correlation between HHQ signal concentrations in sputum and plasma with quantitative P. aeruginosa load in sputum in 59 CF patients with chronic pulmonary P. aeruginosa infection at the start of a pulmonary exacerbation. More specifically, FIG. 7 illustrates the cross sectional association between quantitative load of P. aeruginosa in spontaneous sputum measured using traditional culture techniques and HHQ signal concentration in (i) sputum (N=33), (ii) plasma (N=35) of CF patients at the start of pulmonary exacerbation with chronic pulmonary P. aeruginosa infection. N=number of patients with samples available FIG. 8—illustrates longitudinal data showing change in NHQ signal concentrations (i) sputum, (ii) plasma and (iii) urine in 29 CF patients who are chronically infected with P. aeruginosa at 3 time points: (a) clinically stable, (b) at the start of a pulmonary exacerbation and (c) at the end of systemic anti-pseudomonal therapy for a pulmonary exacerbation.

FIG. 9—illustrates longitudinal data showing the change in HHQ signal concentrations (i) sputum, (ii) plasma and (iii) urine in 29 CF patients who are chronically infected with P. aeruginosa at 3 time points: (a) clinically stable, (b) at the start of a pulmonary exacerbation and (c) at the end of systemic anti-pseudomonal therapy for a pulmonary exacerbation.

FIG. 10—illustrates longitudinal data showing the change in C7-PQS signal concentrations (i) sputum and (ii) plasma in 29 CF patients who are chronically infected with P. aeruginosa at 3 time points: (a) clinically stable, (b) at the start of a pulmonary exacerbation and (c) at the end of systemic anti-pseudomonal therapy for a pulmonary exacerbation.

Figure 11:
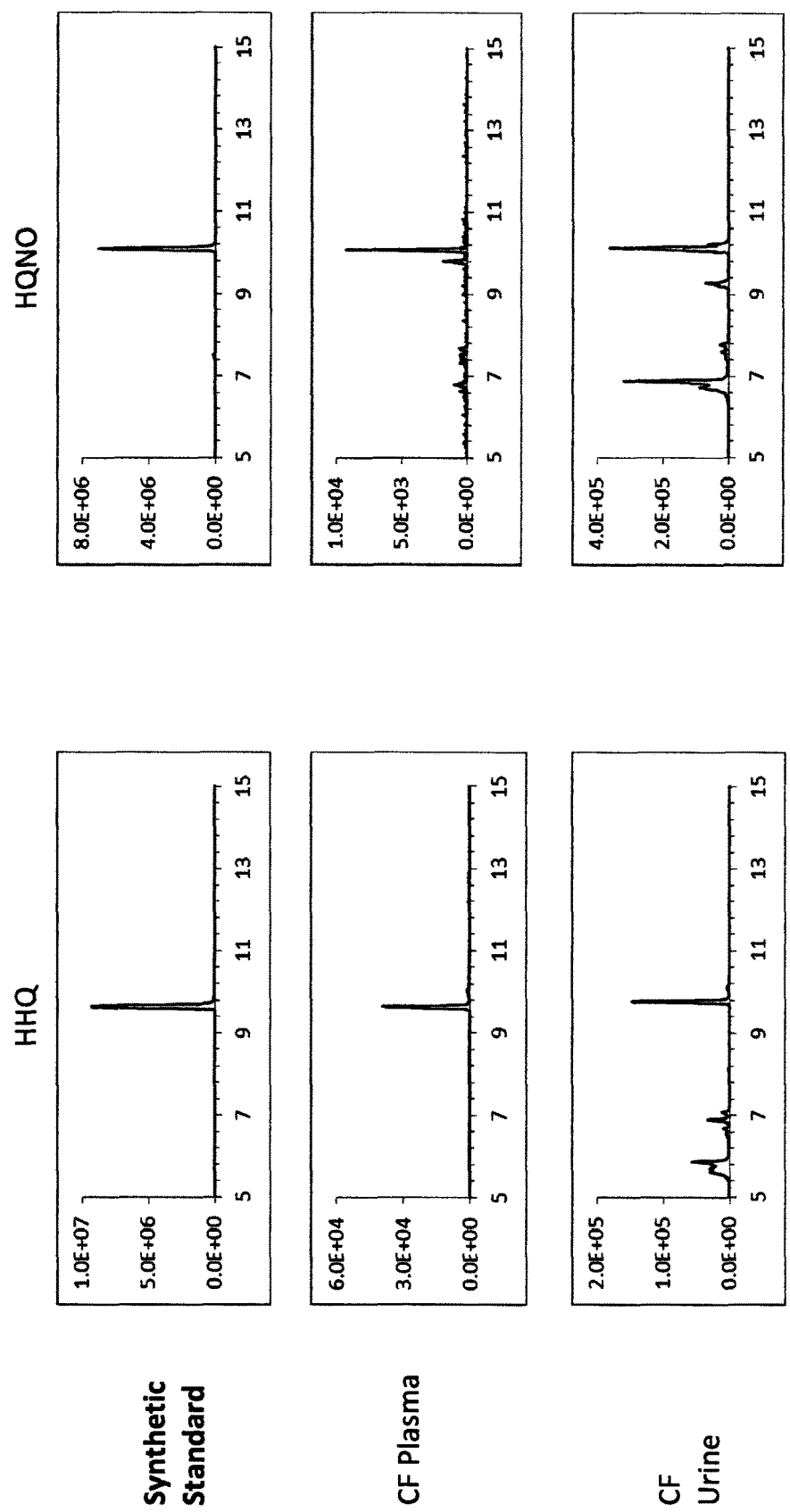
Figure 11:
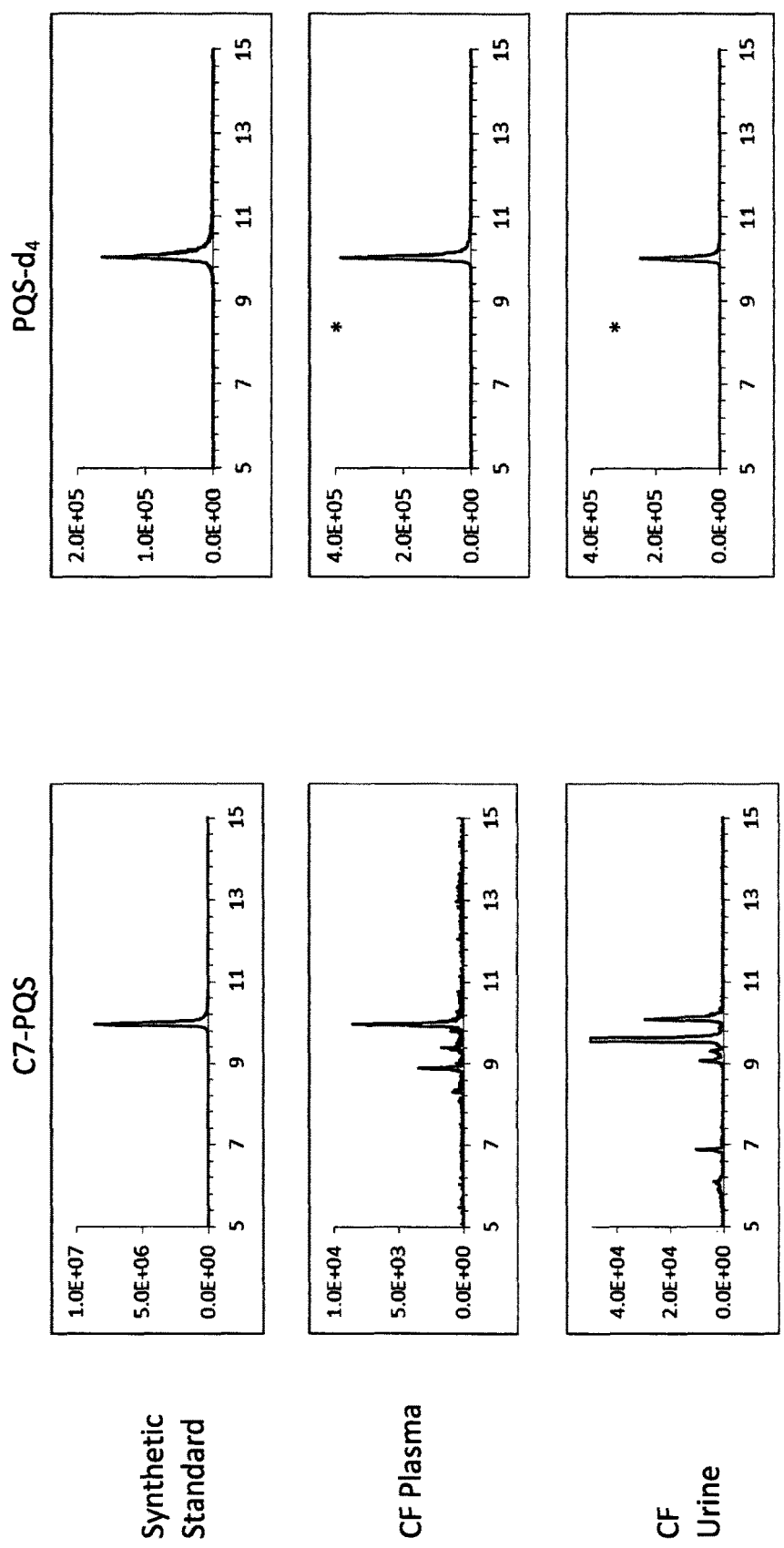

FIG. 11—illustrates representative MRM chromatograms used for the quantitative analysis of un-metabolised HHQ, C7-PQS and HQNO in urine and plasma clinical samples from CF patients. Peaks for these analytes, and the deuterated internal standard, are chromatographically distinct from any interfering peaks indicating the specificity of the LC-MS/MS methodology.

Figure 12:
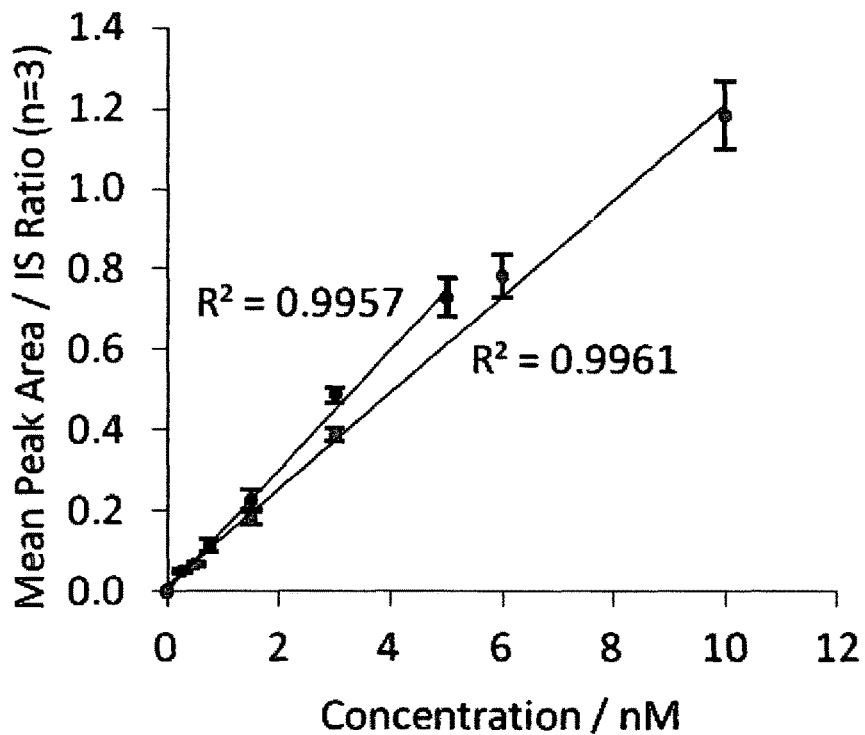
Figure 12:
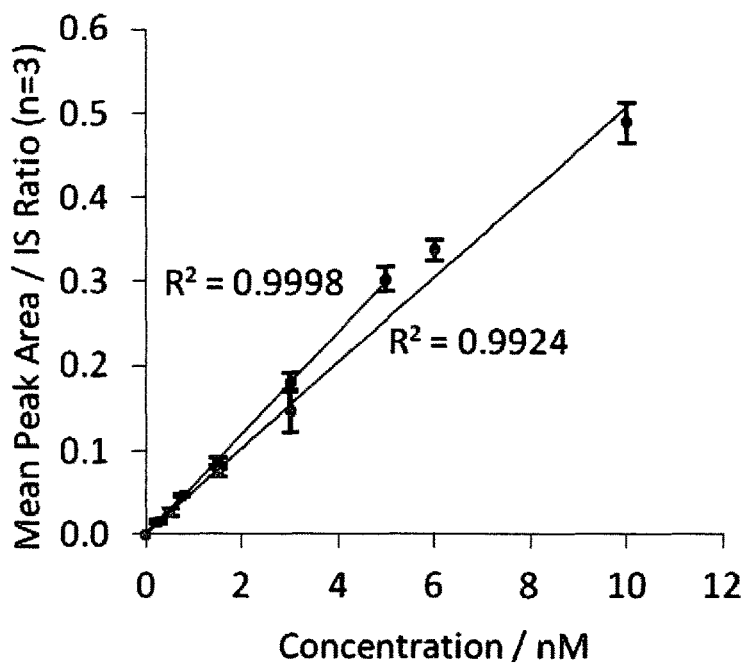
Figure 12:
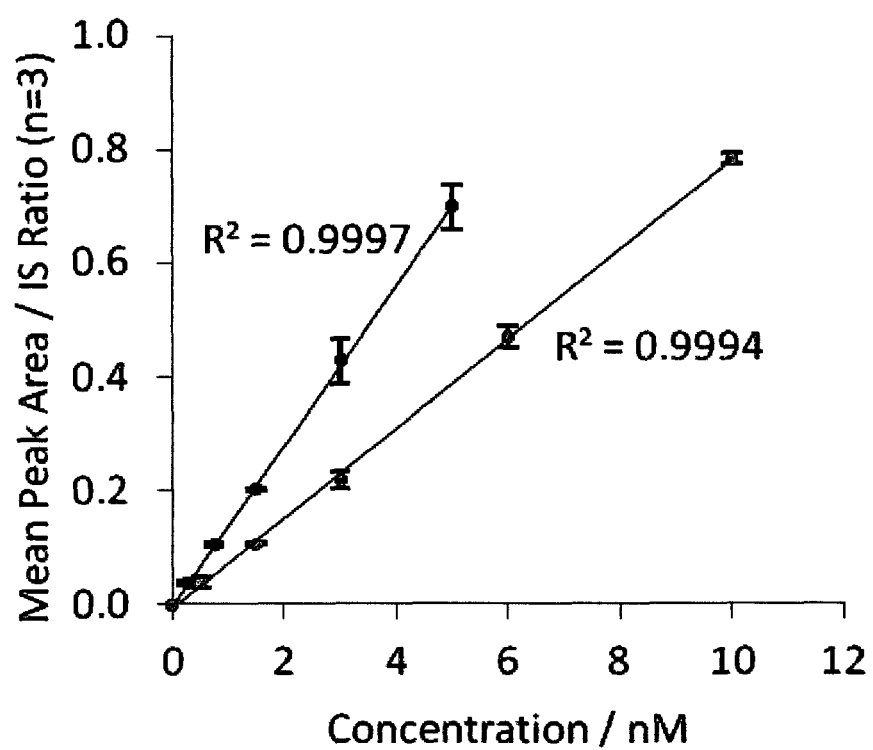

FIG. 12—illustrates representative six-point calibration lines constructed for the quantitative analysis of HHQ, C7-PQS and HQNO in clinical samples. Serial dilutions of A: HHQ, B: HQNO and C: C7-PQS, were spiked into blank plasma (red data points) and urine (black data points), along with an internal standard, prior to solid phase extraction.

FIG. 13—illustrates validation results: calibration intra- and inter-day precision and accuracy of assay method determined at two concentrations in both spiked urine and plasma samples.

Figure 14:
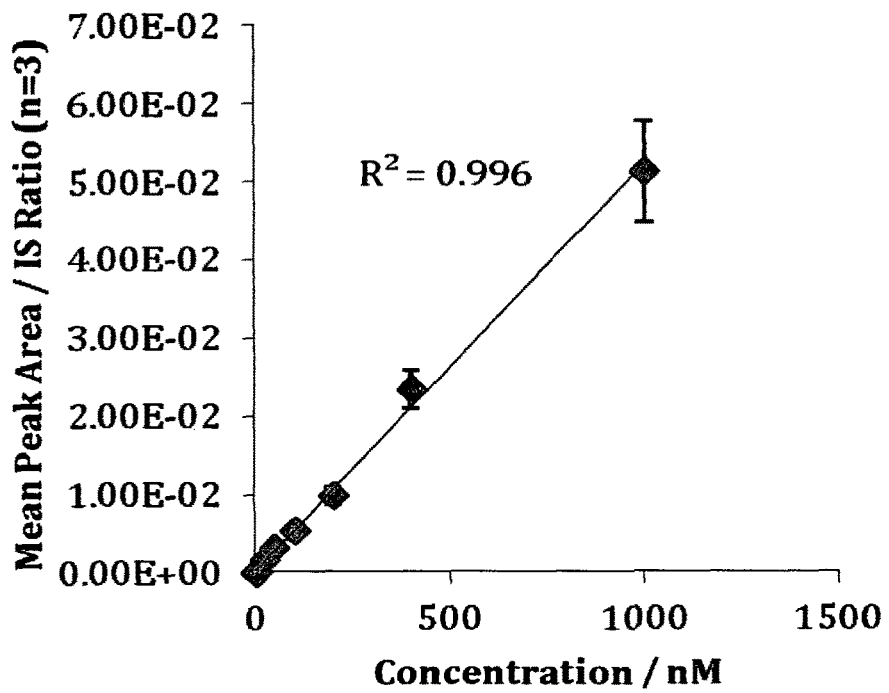
Figure 14:
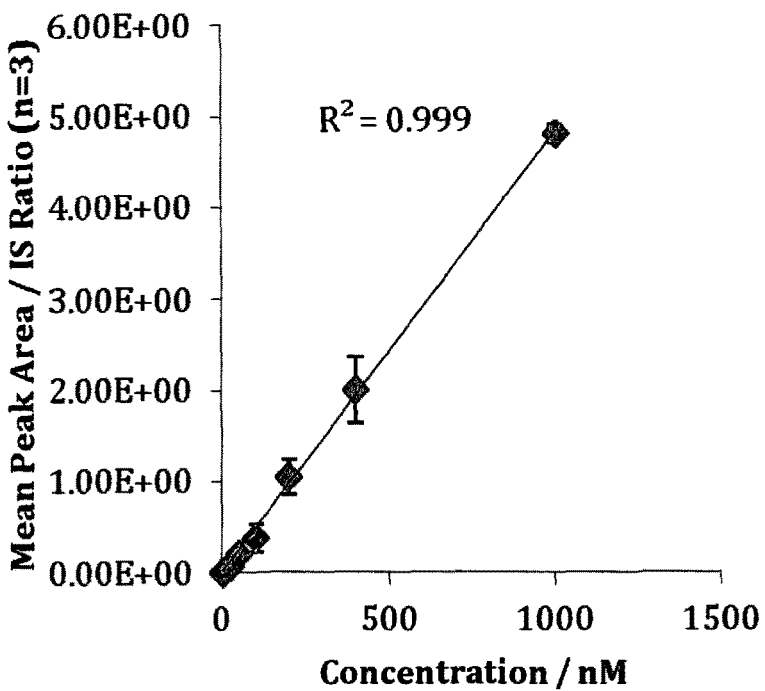
Figure 14:
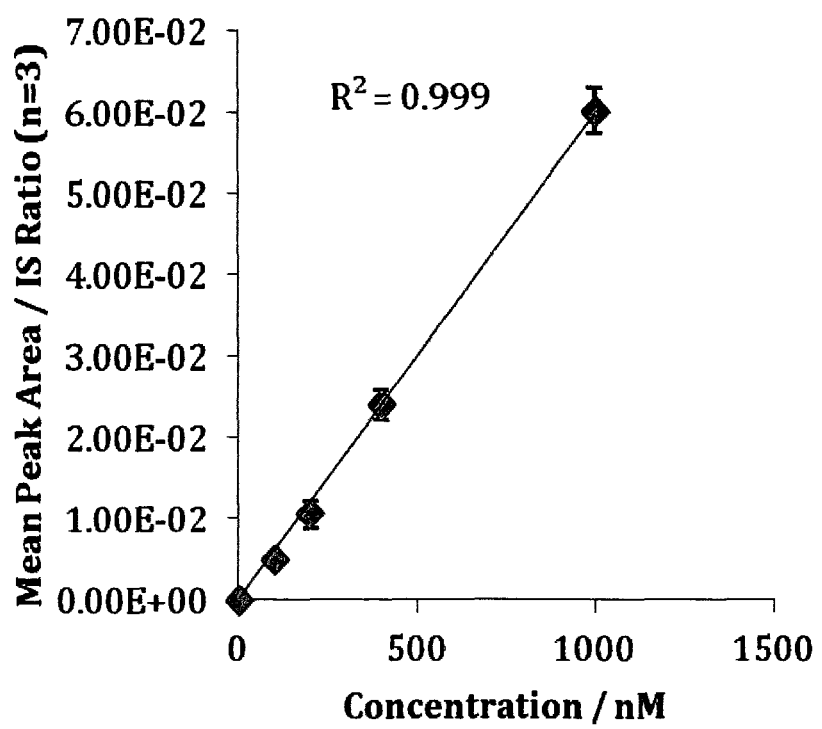

FIG. 14—illustrates representative calibration lines constructed for the quantitative analysis of HHQ, C7-PQS and HQNO in sputum. Serial dilutions of A: HHQ, B: HQNO and C: C7-PQS, were spiked into 1 ml saline along with an internal standard, prior to solvent extraction.

FIG. 15—illustrates validation results: calibration intra- and inter-day precision and accuracy of assay method determined at two concentrations in spiked saline samples used for the quantification of AQs in sputum samples.

Figure 16:
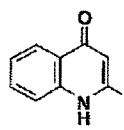

FIG. 16—illustrates the results of the analysis of sputum extracts from six cystic fibrosis patients, all of which were screened for the presence of all possible known alkyl quinolones. All the samples were spontaneous sputum samples obtained from patients with cystic fibrosis who were colonised with P. aeruginosa. ✓ Indicates alkyl quinolone detected, - indicates not detected.

FIG. 17—illustrates the results for the analysis of blood plasma and urine extracts from one cystic fibrosis patient who had been admitted to hospital for intravenous anti-pseudomonal antibiotics for a pulmonary exacerbation. The samples were screened for the presence of the three preferential alkyl quinolones (PQS, HHQ and C7-N oxide) and their known metabolised products. ✓ Indicates alkyl quinolone/metabolite detected, - indicates not detected

PRODUCTION AND IDENTIFICATION OF ALKYL QUINOLONE AND METABOLITES

Microsomal Incubations

A standard incubation mixture (500 µl total volume) of TRIS.HCl Buffer (50 mM, pH=7.5 with 5 mM $MgCl_2$) containing 100 µM of a representative AQ and either an in-situ NADPH generating system (consisting of 0.5 mM NADP, 5.0 mM glucose-6-phosphate and 0.5 units of glucose-6-phosphate dehydrogenase) or 5.0 mM uridine 5'-diphosphoglucuronic acid were pre-equilibrated at 37° C. Pooled human liver microsomes (0.25 mg of protein/incubation) was added and the incubation left to stand at 37° C. for 2 hr. Negative control incubations were performed without the NADPH generating system or by using heat denatured (60° C. for 5 min) microsomal suspension. Enzymatic activity was quenched by the addition of 3 volumes of ice-cold MeOH. Centrifugation (5 min at 13000 r.p.m.) was conducted to sediment precipitated protein. The clarified supernatant was removed and diluted to a total volume of 10 ml prior to analysis by mass spectrometry.

MS Analysis of AQ Metabolites Present in Microsomal Incubations

The exact mass of metabolites was determined using a Thermo Exactive mass spectrometer (Hemel Hempstead, U.K.) in conjunction with a Thermo Accela LC system. Instrument control, data collection and analysis were conducted using Xcalibur software (version 2.1.0). The chromatographic separation was achieved using a Phenomenex (Macclesfield, U.K.) Gemini C18 reversed-phase column (3.0 µm, 100×3.0 mm) with an appropriate guard column, maintained at 50° C., using a mobile phase flow rate set at 450 µl/min. Mobile phases consisted of aqueous 0.1% (v/v) formic acid (A) and 0.1% (v/v) formic acid in MeOH (B). The binary gradient began initially at 10% B and ran isocratically for the first 1 min before increasing linearly to 99% B over 9 min. After a further 5 min at this composition, the gradient was returned to 10% B over the next 1 min and allowed to re-equilibrate for 4 min (total run time of 20 min per sample). Sample temperature was maintained at 4° C. in the auto-sampler prior to analysis. The mass spectrometer was operated in positive ionization mode with a heated electrospray ionization (HESI) probe. The electrospray settings were: spray voltage: 4 kV, capillary temperature: 350° C., sheath gas: 40, auxiliary gas: 25, sweep gas: 5 and heater temperature: 350° C.

Multiple reaction monitoring (MRM) and $MS^2$ analysis of metabolites were conducted on a 4000 QTRAP hybrid triple-quadrupole linear ion trap mass spectrometer (Applied Biosystem, Foster City, USA) equipped with a Turbo-Ion source and a Shimadzu series 10AD VP LC system (Shimadzu, Columbia, USA). Analyst software (version 1.4.1) was used for instrument control, data acquisition and processing. Source parameters were set as: curtain gas: 20.0, ion source potential: 5000 V, temperature: 450° C., nebulizer gas: 20.0, and auxiliary gas: 15.0. Analysis was conducted either as a MRM only method or with MRM used as a survey scan to trigger the acquisition of enhanced product ions in an information dependant acquisition (MRM-IDA-EPI). Chromatographic conditions used were as previously described.

Preparation of Urine and Plasma Clinical Samples for Quantitative Analysis

SPE was applied to prepare both urine and plasma samples. SPE cartridges (Waters Oasis hydrophilic-lipophilic balanced (HLB) reversed phase sorbent extraction cartridges, 60 mg) were pre-conditioned with 3 ml of MeOH followed by 3.0 ml of 1% (v/v) AcOH. After the urine or plasma samples, spiked with 10 µl of IS solution (1.0 µmol/L deuterated C7-PQS (PQS-$d_4$) in methanol), diluted and acidified with an equal volume of 1% (v/v) AcOH, were loaded onto the cartridges, they were washed with 2×3 ml of 30% (v/v) MeOH. The retained extracts, eluted from the cartridges with 1.5 ml of MeOH, were dried under vacuum, dissolved in 50 µl of MeOH and stored at −20° C. prior to LC-MS/MS analysis.

Preparation of Calibration Standards and Quality Control Standards for the Quantitative Analysis of AQs in Blood Plasma and Urine.

Blank samples (1.0 ml of urine and 0.5 ml of plasma) from healthy (non-CF) volunteer donors, spiked with 10 µl of IS solution (1.0 µmol/L PQS-$d_4$ in methanol), were further spiked with 50 µl of an AQ mix prepared at a range of concentrations (0, 5, 15, 30, 60 and 100 nM), giving an overall calibration range of 0-5 nM and 0-10 nM for urine and plasma respectively. QC standards were prepared similarly, spiking blank samples with 50 µl of the AQ mix at 10 and 80 nM producing plasma QC samples of 1 and 8 nM, or 0.5 and 4 nM for urine. All calibration and QC standards were prepared in triplicate, extracted and prepared ready for LC-MS/MS analysis as detailed above. The LLOQ was determined using serial dilutions of the AQ mix spiked into blank urine/plasma, with sample preparation and analysis as previously described. Calculated LLOQs in plasma and urine samples were as follows: (plasma) HHQ, 10 pmol/L; NHQ, 10 pmol/L; HQNO, 30 pmol/L; NQNO, 40 pmol/L; C7-PQS, 100 pmol/L; C9-PQS, 100 pmol/L; and (urine) HHQ, 20 pmol/L; NHQ, 10 pmol/L; HQNO, 30 pmol/L; NQNO, 50 pmol/L; C7-PQS, 50 pmol/L; C9-PQS, 50 pmol/L.

Preparation of Sputum Clinical Samples for Quantitative Analysis

Extracts of sputum samples for LC-MS/MS analysis were prepared by solvent extraction. Up to 1.0 mL of 50% (v/v) sputum suspension was spiked with 10 µL of an internal standard (1.0 µmol/L PQS-$d_4$ in methanol), and extracted in triplicate with 0.5 mL volumes of 0.01% (v/v) acetic acid in ethyl acetate. After the addition of acidified solvent the samples were vortex-mixed for approximately 1 min and centrifuged (3 min at 12,000 g) with the analytes of interest partitioning into the organic phase. The combined organic extracts were dried under vacuum.

Preparation of Calibration Standards and Quality Control Standards for the Quantitative Analysis of AQs in Sputum In the absence of available quantities of uninfected sputa with which to generate matrix matched calibration samples, 0.9% (w/w) saline was used as an alternative. 1.0 ml of saline, spiked with 10 µl of IS solution (1.0 µmol/L PQS-$d_4$ in methanol), were further spiked with 50 µl of an AQ mix prepared at a range of concentrations (0, 25, 50, 100, 200, 400 and 1000 nM). QC standards were prepared similarly, spiking blank samples with 50 µl of the AQ mix at 75 and 800. All calibration and QC standards were prepared in triplicate, extracted and prepared ready for LC-MS/MS analysis as detailed above.

CONCLUSIONS

The data presented herein demonstrates that alkyl quinolones and metabolites thereof can be detected in vivo in biological fluids from cystic fibrosis patients with *P. aeruginosa* infection, but not in biological fluids from CF patients without previous infection with this bacterium or negative healthy controls. This provides evidence that alkyl quinolones and metabolites thereof are biomarkers for *P. aeruginosa* infection.

The results presented further demonstrate that the concentrations of alkyl quinolones and metabolites thereof in biological fluids from CF patients correlate with quantitative load of *P. aeruginosa* in the lung, as measured by traditional microbiological culture techniques. Thus alkyl quinolones and metabolites thereof can be used as biomarkers for monitoring efficacy of clinical treatment interventions.

Alkyl quinolones and metabolites thereof can also be detected in vivo from patients with CF with 'early' or 'intermittent' *P. aeruginosa* infection, who are not currently chronically infected with this bacterium. Thus alkyl quinolones and metabolites thereof can be used to facilitate the early detection of *P. aeruginosa* infection, potentially permitting more timely eradication therapy.

These data demonstrate that the concentrations of several alkyl quinolones and metabolites thereof are elevated in biological samples at the start of a pulmonary exacerbation and that they decrease following the administration of systemic anti-pseudomonal antibiotics in CF patients with chronic *P. aeruginosa* infection. This demonstrates that alkyl quinolones and metabolites thereof are systemic markers of the virulence of the bacteria, which correlate with the clinical status in the host.

The invention claimed is:
1. A method of diagnosing and treating a *P. aeruginosa* or related species infection in a subject suspected of having a *P. aeruginosa* or related species infection comprising:
 (a) providing a sample of blood obtained from the subject;
 (b) determining the level of one or more alkyl quinolones produced by *P. aeruginosa* or a related species in the sample;
 (c) comparing the level of the one or more alkyl quinolones in the blood sample with the level of the one or more alkyl quinolones in a reference sample from a subject without the *P. aeruginosa* or related species infection;

(d) diagnosing the subject with *P. aeruginosa* or related species infection when an increased level of the one or more alkyl quinolones is detected in the blood sample as compared to the reference sample; and (e) administering a suitable antibiotic treatment to the diagnosed subject, thereby diagnosing and treating a *P. aeruginosa* or related species infection in the subject, wherein the one or more alkyl quinolones is selected from the group consisting of 2-nonyl-4-hydroxyquinoline (HHQ), 2-heptyl-3-hydroxy-4(1H)-quinolone (C7-PQS), 2-nonyl-3-hydroxy-4(1H)-quinolone (C9-PQS), 2-nonyl-4-hydroxyquinoline (NHQ), 2-heptyl-4-hydroxyquinoline-N-oxide (HQNO), and 2-nonyl-4-hydroxyquinoline N-oxide (NQNO).

2. The method of claim 1, further comprising monitoring the effectiveness of the treatment in the subject;

wherein the level of the one or more alkyl quinolones is determined in a second sample obtained from the subject following treatment; and wherein a reduction in the level of the one or more alkyl quinolones in the second sample indicates that the treatment is effective.

3. The method of claim 1 wherein the level of one or more alkyl quinolones produced by *P. aeruginosa* or a related species in a sample is determined by mass spectrometry, immunoassays or using a biosensor.

4. The method of claim 1 wherein a species related to *P. aeruginosa* is a *Burkholderia* spp.

5. The method of claim 1 wherein the sample of blood is serum.

6. A method of diagnosing and treating a *P. aeruginosa* or related species infection in a subject suspected of having a *P. aeruginosa* or related species infection comprising:

(a) providing a sample of urine obtained from the subject;

(b) determining the level of one or more alkyl quinolones produced by *P. aeruginosa* or a related species in the sample;

(c) comparing the level of the one or more alkyl quinolones in the urine sample with the level of the one or more alkyl quinolones in a reference sample from a subject without the *P. aeruginosa* or related species infection;

(d) diagnosing the subject with *P. aeruginosa* or related species infection when an increased level of the one or more alkyl quinolones is detected in the urine sample as compared to the reference sample; and (e) administering a suitable antibiotic treatment to the diagnosed subject, thereby diagnosing and treating a *P. aeruginosa* or related species infection in the subject, wherein the one or more alkyl quinolones is selected from the group consisting of 2-nonyl-4-hydroxyquinoline (HHQ), 2-heptyl-3-hydroxy-4(1H)-quinolone (C7-PQS), 2-nonyl-3-hydroxy-4(1H)-quinolone (C9-PQS), 2-nonyl-4-hydroxyquinoline (NHQ), 2-heptyl-4-hydroxyquinoline-N-oxide (HQNO), and 2-nonyl-4-hydroxyquinoline N-oxide (NQNO).

7. The method of claim 1, wherein the subject has been diagnosed with cystic fibrosis prior to providing the sample.

8. The method of claim 6, wherein the subject has been diagnosed with cystic fibrosis prior to providing the sample.

9. The method of claim 6, further comprising monitoring the effectiveness of the treatment in the subject;

wherein the level of the one or more alkyl quinolones is determined in a second sample obtained from the subject following treatment; and wherein a reduction in the level of the one or more alkyl quinolones in the second sample indicates that the treatment is effective.

10. The method of claim 6, wherein the level of one or more alkyl quinolones produced by *P. aeruginosa* or a related species in a sample is determined by mass spectrometry, immunoassays or using a biosensor.

11. The method of claim 6, wherein a species related to *P. aeruginosa* is a *Burkholderia* spp.

\* \* \* \* \*

UNITED STATES PATENT AND TRADEMARK OFFICE
CERTIFICATE OF CORRECTION

PATENT NO. : 10,139,406 B2
APPLICATION NO. : 14/891242
DATED : November 27, 2018
INVENTOR(S) : Miguel Camara et al.

Page 1 of 1

It is certified that error appears in the above-identified patent and that said Letters Patent is hereby corrected as shown below:

In the Claims

At Column 17, Claim number 1, Line numbers 10-11, replace "2-nonyl-4-hydroxyquinoline (HHQ)" with --2-hepyl-4-hydroxyquinoline (HHQ)--.

At Column 18, Claim number 6, Line numbers 13-14, replace "2-nonyl-4-hydroxyquinoline (HHQ)" with --2-hepyl-4-hydroxyquinoline (HHQ)--.

Signed and Sealed this
Twenty-second Day of January, 2019

Andrei Iancu
*Director of the United States Patent and Trademark Office*